United States Patent
Forsberg

(10) Patent No.: US 9,561,004 B2
(45) Date of Patent: Feb. 7, 2017

(54) AUTOMATED 3-D ORTHOPEDIC ASSESSMENTS

(71) Applicant: Sectra AB, Linköping (SE)

(72) Inventor: Daniel Forsberg, Linköping (SE)

(73) Assignee: Sectra AB, Linkoping (SE)

( * ) Notice: Subject to any disclaimer, the term of this patent is extended or adjusted under 35 U.S.C. 154(b) by 537 days.

(21) Appl. No.: 14/013,189

(22) Filed: Aug. 29, 2013

(65) Prior Publication Data

US 2014/0323845 A1 Oct. 30, 2014

Related U.S. Application Data

(60) Provisional application No. 61/817,074, filed on Apr. 29, 2013.

(51) Int. Cl.
| | |
|---|---|
| *G06K 9/00* | (2006.01) |
| *A61B 5/00* | (2006.01) |
| *G06F 19/00* | (2011.01) |
| *G06T 7/00* | (2006.01) |
| *G06T 7/60* | (2006.01) |

(52) U.S. Cl.
CPC ......... *A61B 5/4561* (2013.01); *G06F 19/3437* (2013.01); *G06T 7/0014* (2013.01); *G06T 7/0036* (2013.01); *G06T 7/0046* (2013.01); *G06T 7/60* (2013.01); *G06T 2207/10072* (2013.01); *G06T 2207/20016* (2013.01); *G06T 2207/30012* (2013.01)

(58) Field of Classification Search
CPC .......... G06K 9/00; G06K 9/34; A61B 5/4561; G06F 19/3437; G06T 7/0014; G06T 7/0036; G06T 7/0046; G06T 7/60; G06T 2207/30012; G06T 2207/10072; G06T 2207/20016
See application file for complete search history.

(56) References Cited

U.S. PATENT DOCUMENTS

| | | | | |
|---|---|---|---|---|
| 2006/0120583 | A1* | 6/2006 | Dewaele | G06T 3/0068 382/128 |
| 2007/0081712 | A1* | 4/2007 | Huang | G06T 7/0028 382/128 |
| 2011/0058720 | A1* | 3/2011 | Lu | G06T 7/0032 382/131 |
| 2012/0027271 | A1* | 2/2012 | Zankowski | G06T 7/0081 382/128 |
| 2012/0143090 | A1* | 6/2012 | Hay | A61B 6/505 600/587 |

OTHER PUBLICATIONS

Adam et al. "Automatic Measurement of Vertebral Rotation in Idiopathic Scoliosis", *Spine*, 31, 2006, E80-E83.

Delorme et al. "Assessment of the 3-D Reconstruction and High-Resolution Geometrical Modeling of the Human Skeletal Trunk From 2-D Radiographic Images", *IEEE Transactions on Biomedical Engineering*, vol. 50, No. 8, Aug. 2003, 989-998.

(Continued)

*Primary Examiner* — Elmer Chao
(74) *Attorney, Agent, or Firm* — Myers Bigel, P.A.

(57) ABSTRACT

Systems, methods, computer programs, and circuits can perform automated spinal assessments using a 3-D model and a 3-D patient image data set of the spine which do not rely on vertebral symmetry.

35 Claims, 9 Drawing Sheets
(3 of 9 Drawing Sheet(s) Filed in Color)

(56) References Cited

OTHER PUBLICATIONS

Duong et al. "Three-Dimensional Classification of Spinal Deformities Using Fuzzy Clustering", *Spine*, 2006;31:923-930.
Easwar et al. "Does lateral vertebral translation correspond to Cobb angle and relate in the same way to axial vertebral rotation and rib hump index? A radiographic analysis on idiopathic scoliosis", *Eur Spine J.*, 20, 2011, 1095-1105.
Eklund et al. "Phase Based Volume Registration Using CUDA", *2010 IEEE International Conference on Acoustics Speech and Signal Processing (ICASSP)*, Mar. 14-19, 2010, 658-661.
Fang et al. "Tetrahedral mesh generation from volumetric binary and grayscale images", *IEEE International Symposium on Biomedical Imaging: From Nano to Macro, 2009. ISBI '09.* 1142-1145.
Forsberg et al. "Fully automatic measurements of axial vertebral rotation for assessment of spinal deformity in idiopathic scoliosis", *Phys Med. Biol.*, Mar. 21, 2013, 58(6):1776-87.
Forsberg et al. "Phase-Based Non-Rigid 3D Image Registration: From Minutes to Seconds Using CUDA", *Joint MICCAI Workshop on High Performance and Distributed Computing for Medical Imaging, HP-MICCAI / MICCAI-DCI 2011*, Sep. 22, 2011,Toronto, Canada, 10 pages.
Hemmendorff et al. "Phase-Based Multidimensional Volume Registration", *IEEE Transactions on Medical Imaging*, vol. 21, No. 12, Dec. 2002, 1536-1543.
Hong et al. "Evaluation of the Three-Dimensional Deformities in Scoliosis Surgery With Computed Tomography", *Spine*, vol. 36, No. 19, pp. E1259-E1265, 2011.
Janssens et al. "Diffeomorphic Registration of Images with Variable Contrast Enhancement", *International Journal of Biomedical Imaging*, vol. 2011, Article ID 891585, 16 pages, Received Apr. 30, 2010.
Kadoury et al. "Classification of three-dimensional thoracic deformities in adolescent idiopathic scoliosis from a multivariate analysis", *Eur Spine J.*, 21, 2012, 40-49.
Kalra et al. "Whole spine CT for evaluation of scoliosis in children: feasibility of sub-milliSievert scanning protocol", *Acta Radiol*, 2013, 54:226-230.
Kay "Feature Discovery under Contextual Supervision using Mutual Information", *International Joint Conference on Neural Networks, 1992, IJCNN*, vol. 4, Jun. 7-11, 1992.
Kim et al. "A fully automatic vertebra segmentation method using 3D deformable fences", *Computerized Medical Imaging and Graphics*, 33, 2009, 343-352.
Knutsson et al. "Morphons: Segmentation Using Elastic Canvas and Paint on Priors", *IEEE International Conference on Image Processing, ICIP 2005*, Sep. 11-14, 2005, vol. 2, 1226-1229.
Sangole et al. "Three-Dimensional Classification of Thoracic Scoliotic Curves", *Spine*, 2009;34:91-99.
Schwab et al. "Adult Scoliosis, A Quantitative Radiographic and Clinical Analysis", *Spine*, 27, 2002, 387-392.
Segars et al. "4D XCAT phantom for multimodality imaging research", *Med. Phys.*, 37, (9), Sep. 2010, 4902-4915.
Thirion "Image matching as a diffusion process: an analogy with Maxwell's demons", *Medical Image Analysis*, 1998, vol. 2, No. 3, pp. 243-260.
Vercauteren et al. "Symmetric Log-Domain Diffeomorphic Registration: A Demons-Based Approach", *Med Imgage Comput Comput Assist Interv.*, 2008, 11 (Part 1), 754-761.
Vrtovec et al. "Determination of axial vertebral rotation in MR images: comparison of four manual and a computerized method", *European Spine Journal*, 19, 2010, 774-781.
Klinder et al. "Automated model-based vertebra detection, identification, and segmentation in CT images", *Medical Image Analysis*, vol. 13, 471-482, 2009.
Stern et al. "Parametric modeling and segmentation of vertebral bodies in 3D CT and MR spine images", *Phys. Med. Biol.*, vol. 56, 7505-7522, 2011.

\* cited by examiner

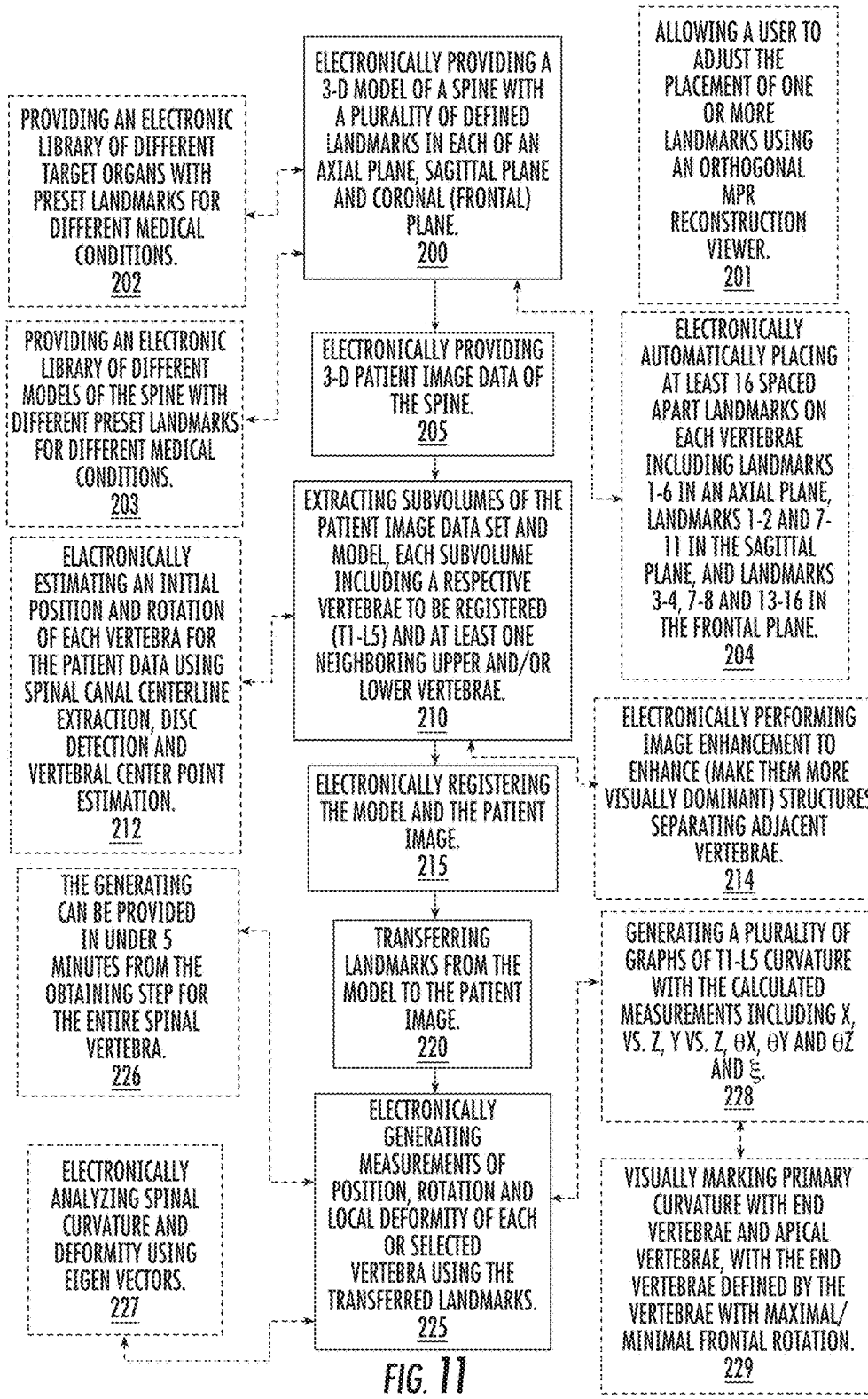

AUTOMATED 3-D ORTHOPEDIC ASSESSMENTS

RELATED APPLICATIONS

This application claims the benefit of and priority to U.S. Provisional Application Ser. No. 61/817,074, filed Apr. 29, 2013, the contents of which are hereby incorporated by reference as if recited in full herein.

FIELD OF THE INVENTION

The invention relates to automated assessments of anatomical structures and may be particularly suitable for evaluating deformity measurements associated with three dimensional (volumetric) image data sets of the spine.

BACKGROUND

Assessing spinal deformity is of tremendous importance for a number of diseases affecting the human spine; one of them is scoliosis and its most common type, idiopathic scoliosis. Scoliosis is a disease that affects the human spine by introducing an abnormal lateral curvature, as observed in the frontal plane. The disease is typically detected during a standard physical examination. The routine procedure for assessing the severity of curvature is to use an anterior-posterior radiograph, where the Cobb angle is measured. See, R. Cobb, "Outline for study of scoliosis," American Academy of Orthopedic Surgeons, Instructional Course Lectures, pp. 261-75, 1948. The Cobb angle is defined as the angle between the end vertebrae of the scoliotic curvature. There are other manual measurement methods for assessing frontal curvature and also sagittal curvature of the spine, but the Cobb angle is the most commonly used measure. The Cobb angle plays a significant role both when monitoring the disease and when selecting the appropriate treatment (bracing or surgery), even though it is well-established that the Cobb angle is insufficient both to describe and to properly quantify the deformity in scoliosis. This is due to the three dimensional (3D) nature of a scoliotic curvature, which may include a displacement, a rotation and/or a deformation of each vertebra. The Cobb angle particularly fails to measure the axial vertebral rotation, considered to be important for the assessment of spinal deformity in scoliosis.

Another limitation of the Cobb angle is its observer variability. Hence, other approaches for quantifying the degree of scoliosis are called for, including not only new quantitative measures but more importantly an analysis determining how different measures relate to each other and to the clinical outcome. See, Schwab et al., "Adult scoliosis: a quantitative radiographic and clinical analysis," Spine, vol. 27, no. 4, pp. 387-392, 2002; Hong et al., "Evaluation of the three-dimensional deformities in scoliosis surgery with computed tomography: Efficacy and relationship with clinical outcomes," Spine, vol. 36, no. 19, pp. E1259-E1265, 2011; and Easwar et al., "Does lateral vertebral translation correspond to Cobb angle and relate in the same way to axial vertebral rotation and rib hump index? A radiographic analysis on idiopathic scoliosis," European Spine Journal, vol. 20, no. 7, pp. 1095-1105, 2011. This relationship of the different measures can be important in order to classify various sub-types of idiopathic scoliosis and to determine suitable treatments of the different sub-types.

There remains a need for automated methods which can reliably assess the 3D deformity of the spine in individual patients.

SUMMARY OF EMBODIMENTS OF THE PRESENT INVENTION

Embodiments of the invention provide automated measurements of parameters of target organs using a 3-D model, landmarks and a 3-D image data set.

The measurements can include position, rotation and deformation of a target organ using a 3-D model and a 3-D patient image data set which does not rely on (e.g., vertebral) symmetry of the target organ.

Embodiments of the invention are directed to methods of providing automated measurements associated with anatomical features of a spine. The methods include: (a) electronically providing a three dimensional (3-D) model of the spine having substantially naturally shaped vertebrae, with a plurality of landmarks electronically applied to each of the vertebrae; (b) obtaining 3-D patient image data of a spine of the patient; (c) extracting subvolumes of the 3-D patient image data associated with the spine, respective subvolumes each including at least one vertebra in full and at least one neighboring vertebrae structure or a portion thereof; (d) extracting subvolumes of the 3-D model corresponding to the subvolumes of the patient image data (e) electronically registering, subvolume by subvolume, the 3-D model and the 3-D patient image data of the spine; then (f) electronically transferring the landmarks from the model to the 3-D patient image; and (g) electronically calculating measurements for one or more vertebrae, including at least one of the following: (i) position in x, y and z coordinates (mm), (ii) rotation $\theta x$, $\theta y$, $\theta z$ in degrees, and (iii) a local deformity (lateral wedge) value (mm) using the transferred landmarks.

The method can include electronically enhancing respective vertebra features in the subvolumes of the patient image data before electronically registering corresponding subvolumes of the model and the patient image data.

Each vertebra may include landmarks 1-6 defining the axial plane, landmarks 1-2 and 7-11 defining the sagittal plane and landmarks 3-4, 7-8 and 13-16 defining the coronal plane.

The registration can be carried out by first applying an affine registration for each vertebra, then applying a deformable registration for each vertebra.

Before the registration, the method may optionally include pre-processing the patient image data to electronically estimate an initial position and rotation of each vertebrae of the patient image data by (i) calculating a spinal canal centerline, detecting disc location, (ii) calculating an initial rotation, then (iii) calculating an estimate of vertebrae center points, then (iv) adjusting vertebral rotation using the estimated center points and generating an adjusted estimated spine shape with an estimated location and rotation of the respective vertebrae of the patient data using the adjusted estimated rotation.

The method can include electronically generating a plurality of graphs of T1-L5 curvature using the calculated measurements, including graphs of displacements (mm) x vs. z and y vs. z, a graph of the calculated local deformity (mm) vs. z and at least one graph of a respective rotational measurement of one or more of rotation $\theta_x$, $\theta_y$, $\theta_z$ in degrees vs. z.

The local deformity can be electronically calculated based on a vertebral height difference of vertebral height measurements between defined pairs of landmarks.

The local deformity can be electronically calculated based on an angle between planes fitted to superior and inferior endplates.

The method can include electronically generating graphs that illustrate a primary curvature that is defined with visually marked end vertebrae and an apical vertebrae with the end vertebrae defined by maximal and minimal frontal rotation $\theta_y$.

The method can include electronically generating an estimated Cobb angle using the estimated measurements.

The x, y and z coordinates of each vertebrae can be calculated using an average of coordinates of the transferred landmarks of a respective vertebrae.

Rotation θx, θy, θz in degrees can be calculated as Euler angles, using a fixed world frame, derived from rotation matrix $R=R_Z(\theta_Z)R_Y(\theta_Y)R_X(\theta_X)$, wherein $\theta_Z$ corresponds to: $\theta_Z$ corresponds to axial vertebral rotation, $\theta_Y$ corresponds to frontal rotation and $\theta_X$ corresponds to sagittal rotation.

The method can include electronically generating statistical models of spinal curvature of groups of different patients using Eigenvector analysis of the calculated measurements.

The method can include evaluating whether a patient has idiopathic scoliosis and/or for quantifying an extent or configuration of the idiopathic scoliosis based on the calculated measurements.

The electronic transfer of the landmarks can be carried out using an electronically calculated estimated transformation that can evaluate both symmetric and asymmetric vertebrae of the 3-D patient image data.

The electronic registering can be carried out using phase-based registration.

The electronic providing of the three dimensional (3-D) model of the spine having substantially naturally shaped vertebrae can be carried out to have vertebrae at all levels, T1-L5.

The method can include allowing a user to electronically define placement of the landmarks using a GUI and display presenting the 3-D model.

The electronic providing of the three dimensional (3-D) model of the spine having substantially naturally shaped vertebrae with the landmarks can be carried out by providing a menu of selectable landmark sets and allowing a user to select one or more of the landmark sets for use.

The electronic providing of the three dimensional (3-D) model of the spine having substantially naturally shaped vertebrae with the landmarks can be carried out by providing the 3-D model with a default set of landmarks.

The method can include allowing a user to electronically adjust location of landmarks and/or add or remove one or more landmarks.

The electronic providing of the three dimensional (3-D) model of the spine having substantially naturally shaped vertebrae with the landmarks can be carried out by providing a first landmark set for a first set of the calculated measurements and a second landmark set for a second set of calculated measurements.

The patient images can be time-resolved images for generating visual output of curvature change over time thereby allowing monitoring of progression of a disease, change associated with a therapy or allowing visualizations and associated calculated measurements associated with changes in spinal structure between images taken in different positions of a patient.

Other embodiments are directed to clinician workstations. The workstations include: at least one display; and a circuit in communication with the at least one display. The circuit includes or is in communication with at least one processor configured to: (i) provide a three-dimensional (3-D) model of the spine having substantially naturally shaped vertebrae, with a plurality of landmarks electronically applied to each of the vertebrae; (ii) obtain 3-D patient image data of a spine of the patient; (iii) extract subvolumes of the 3-D patient image data associated with the spine, respective subvolumes each including at least one vertebra in full and at least one neighboring vertebrae structure or a portion thereof; (iv) extract subvolumes of the 3-D model corresponding to the subvolumes of the patient image data; (v) register, subvolume by subvolume, the 3-D model and the 3-D patient image data of the spine; then (vi) transfer the landmarks from the model to the 3-D patient image; and (vii) calculate measurements for one or more vertebrae, including at least one of the following: (a) position in x, y and z coordinates (mm), (b) rotation θx, θy, θz in degrees, and (c) a local deformity (lateral wedge) value (mm) using the transferred landmarks.

The at least one processor of the circuit can be configured to carry out image enhancement of respective vertebra features in the subvolumes of the patient image data before electronically registering corresponding subvolumes of the model and the patient image data.

Each vertebra in the 3-D model comprises respective landmarks residing in each of an axial plane, a sagittal plane and a coronal plane.

Each vertebra in the 3-D model comprises landmarks 1-6 defining the axial plane, landmarks 1-2 and 7-11 defining the sagittal plane and landmarks 3-4, 7-8 and 13-16 defining the coronal plane.

The at least one processor can be configured to register subvolume by subvolume, the 3-D model and the 3-D patient image data of the spine by (i) first applying an affine registration for each vertebra, then (ii) applying a deformable registration for each vertebra.

The at least one processor of the circuit can be configured to pre-process the 3-D patient image data to estimate an initial position and rotation of each vertebrae of the patient image data by (i) calculating a spinal canal centerline, detecting disc location, (ii) calculating an initial rotation, then (iii) calculating an estimate of vertebrae center points, then (iv) adjusting vertebral rotation using the estimated center points and generating an adjusted estimated spine shape with an estimated location and rotation of the respective vertebrae of the patient data using the adjusted estimated rotation. The at least one processor can be configured to register the 3-D model and the 3-D patient image data of the spine using the generated adjusted estimated spine shape.

The at least one processor of the circuit can be configured to generate a plurality of graphs of T1-L5 curvature using the calculated measurements, including graphs of displacements (mm) x vs. z and y vs. z, a graph of the calculated local deformity (mm) vs. z, and at least one graph of a respective rotational measurement of one or more of rotation θx, θy, θz in degrees vs. z.

The at least one processor of the circuit can be configured to calculate the local deformity based on a vertebral height difference of vertebral height measurements between defined pairs of landmarks.

The at least one processor of the circuit can be configured so that local deformity is electronically calculated based on an angle between planes fitted to superior and inferior endplates.

The at least one processor of the circuit can be configured to generate a plurality of graphs that illustrate a primary curvature that is defined with visually marked end vertebrae and an apical vertebrae with the end vertebrae defined by maximal and minimal frontal rotation θy.

The at least one processor of the circuit can be configured to generate an estimated Cobb angle measurement using the estimated measurements.

The at least one processor of the circuit can be configured to generate a plurality of graphs wherein the x, y and z coordinates of each vertebrae are calculated using an average of coordinates of the transferred landmarks of a respective vertebrae.

Rotation $\theta_x$, $\theta_y$, $\theta_z$ in degrees are calculated as Euler angles, using a fixed world frame, derived from rotation matrix $R=R_Z(\theta_Z)R_Y(\theta_Y)R_X(\theta_X)$, wherein $\theta_Z$ corresponds to axial vertebral rotation, $\theta_Y$ to frontal rotation, and $\theta_X$ to sagittal rotation.

The at least one processor of the circuit can be configured to generate statistical models of spinal curvature of groups of different patients using Eigenvector analysis of the calculated measurements.

The electronic transfer of the landmarks can be carried out using an electronically calculated estimated transformation that can evaluate both symmetric and asymmetric vertebrae of the 3-D patient image data.

The registration can be carried out using phase-based registration.

The three dimensional (3-D) model of the spine can have substantially naturally shaped vertebrae has vertebrae at all levels, T1-L5.

The at least one processor of the circuit can allow a user to electronically define placement of the landmarks using a GUI and display presenting the 3-D model.

The landmarks can be provided using a menu of selectable landmark sets and allowing a user to select one or more of the landmark sets for use.

The landmarks can be provided on the 3-D model as a default set of landmarks.

The 3-D model can be configured to allow a user to electronically adjust location of landmarks and/or add or remove one or more landmarks.

The 3-D model of the spine can be provided with or a user can select one or both of a first landmark set for a first set of the calculated measurements and a second landmark set for a second set of calculated measurements.

The 3-D patient images can be time-resolved images for generating visual output of curvature change over time thereby allowing monitoring of progression of a disease, change associated with a therapy or allowing visualizations and associated calculated measurements associated with changes in spinal structure between images taken in different positions of a patient.

Still other embodiments are directed to systems for evaluating spinal patient image data. The systems include: at least one processor comprising a spinal deformity analysis module; and at least one display in communication with the at least one processor. The spinal deformity analysis module is configured to: (a) provide a three dimensional (3-D) model of the spine having substantially naturally shaped vertebrae to the display, the 3-D model configured to allow a user to apply or have a plurality of landmarks electronically applied to each of the vertebrae; (b) obtain 3-D patient image data of a spine of the patient; (c) register the 3-D model and the 3-D patient image data of the spine; then (d) transfer the landmarks from the model to the 3-D patient image; then (e) calculate measurements for the vertebrae, including a plurality of the following: (i) position in x, y and z coordinates (mm), (ii) rotation θx, θy, θz in degrees, and (iii) a local deformity (lateral wedge) value (mm) using the transferred landmarks; and (f) generate a plurality of graphs of curvature of the spine to the display using the calculated measurements.

The graphs and calculated measurements can be computed rapidly in between 2-10 minutes for all vertebrae, measured from a time when the patient image data set is obtained.

The spinal deformity analysis module can be held by at least one server that communicates with a circuit in communication with the at least one display via an intranet or the Internet, and wherein the system comprises a picture, archiving and communication system that obtains the 3-D patient image data for the spinal deformity analysis module.

The spinal deformity analysis module can be configured to: (i) extract subvolumes of the 3-D patient image data associated with the spine, respective subvolume each including at least one vertebra in full and at least one neighboring vertebrae structure or a portion thereof, (ii) extract subvolumes of the 3-D model corresponding to the subvolumes of the patient image data; then (iii) register, subvolume by subvolume, the 3-D model and the 3-D patient image data of the spine.

Each vertebra in the 3-D model comprises landmarks 1-6 defining the axial plane, landmarks 1-2 and 7-11 defining the sagittal plane and landmarks 3-4, 7-8 and 13-16 defining the coronal plane.

The spinal deformity analysis module can be configured to register the 3-D model to the 3-D patient image data by (i) first applying an affine registration for each vertebra, then (ii) applying a deformable registration for each vertebra.

Still other embodiments are directed to a computer program product for analyzing image data sets. The computer program product includes a non-transitory computer readable storage medium having computer readable program code embodied in the medium. The computer-readable program code includes computer readable program code configured to carry out the method of claim 1.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A illustrates an optional "pre-processing" method according to embodiments of the present intention.

The top panels in FIG. 2A illustrate a patient's spine. The bottom panels in FIG. 2A illustrate a 3-D model of the spine. The upper and lower left panels of FIG. 2B illustrate a subvolume extraction of the patient data and spine model for a respective vertebra according to embodiments of the present invention. The remaining panels illustrate affine and deformable registrations on the subvolumes according to embodiments of the present invention. FIG. 2C illustrates the patient image of the full spine with landmarks transferred from the 3-D model according to embodiments of the present invention.

FIG. 3A is a mid-axial view of a respective vertebra. FIG. 3B is a mid-sagittal view of the respective vertebra. FIG. 3C is a mid-frontal view of the respective vertebra.

FIG. 11 is a flow chart of exemplary actions that can be used to carry out methods according to embodiments of the present invention.

DETAILED DESCRIPTION OF EMBODIMENTS OF THE INVENTION

Figure 1:
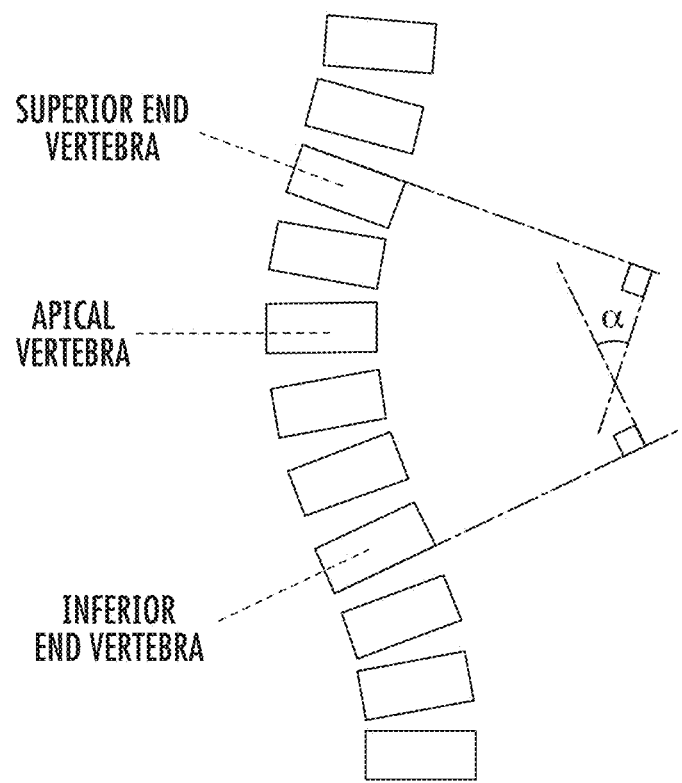
FIG. 1 is a schematic illustration of a Cobb angle that can be measured as the angle between two lines drawn parallel to the upper and lower endplates of two end vertebrae in the scoliotic curvature.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "about" means that the recited parameter may vary somewhat from the recited value, typically within +/−20% or +/−10%.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "circuit" refers to an entirely software embodiment or an embodiment combining software and hardware aspects, features and/or components (including, for example, at least one processor and software associated therewith embedded therein and/or executable by and/or one or more Application Specific Integrated Circuits (ASICs), for programmatically directing and/or performing certain described actions or method steps). The circuit can reside in one location or multiple locations, it may be integrated into one component or may be distributed, e.g., it may reside entirely in a workstation or single computer, partially in one workstation, cabinet, or computer, or totally in a remote location away from a local display at a workstation.

The term "visualization" means to present images to a user or users for viewing. The visualization can be in a flat 2-D image and/or in 2-D that appears to be 3-D images on a display, data representing features (physical, electrical or magnetic and the like) with different visual characteristics such as with differing intensity, opacity, color, texture and the like. The actual visualization can be shown on a screen or display so that the volume or region (e.g., map, or topographical or anatomical structure) is in a flat 2-D and/or in 2-D that appears to be 3-D volumetric images with data representing features or electrical output with different visual characteristics such as with differing intensity, opacity, color, texture and the like.

The term "time-resolved" 3-D" images means images derived from data sets taken at different time-points and/or at different patient positions (bending). Time-resolved 3-D images can be used to monitor the progress of the disease over time and/or to visualize changes between images taking while a patient is in different positions.

The term "GPU" refers to a Graphic Processing Unit which is typically at least one processor that can be used with a CPU.

The term "affine registration" refers to a mathematical (computational) correction for general translation, rotation and scale differences between the model and the 3-D patient image data.

The term "deformable registration" refers to a registration that mathematically (computationally) fits the 3-D model to the 3-D patient data.

Embodiments may be particularly suitable for use with medical image data sets from any imaging modality including MRI and CT. The images may optionally be generated using Direct Volume Rendering (DVR). DVR, a term well-known to those of skill in the art, comprises electronically rendering a medical image directly from data sets to thereby display visualizations of target regions of the body, which can include color as well as internal structures, using three-dimensional (3D) or time-resolved 3D data. In contrast to conventional iso-surface graphic constructs, DVR does not require the use of intermediate graphic constructs (such as polygons or triangles) to represent objects, surfaces and/or boundaries. However, DVR can use mathematical models to classify certain structures and can use graphic constructs.

The term "automatically" means that the operation can be substantially, and typically entirely, carried out without human or manual input, and is typically programmatically directed or carried out. The term "electronically" includes both wireless and hard-wired connections between components.

The term "clinician" means physician, radiologist, physicist, coroner, medical examiner, forensic pathologist or other personnel desiring to review medical data of a patient, which is typically a live human or animal patient, but the subject may be deceased.

The term "adaptive" means measurements of different parameters of the target bone structure, e.g., vertebraes, can be readily adapted from one or more defined measurements to other measures by changing the set of defined landmarks used.

The term "landmark" and derivatives thereof refer to electronic tags or markings that can be attached to structure associated with a model of an organ and/or patient image data of an organ, e.g., the spine. The landmarks can be electronically attached to a location in and/or on a model or in or on a feature in patient image data and subsequently electronically registered or correlated to a corresponding position or location in a like structure in a patient image, visualization and/or model, typically using one or more defined coordinate systems.

The term "subvolume" refers to a predefined target feature or component of a 3D model or image data of a 3D patient image data set. In some embodiments, each subvolume includes at least one vertebra in full and at least one neighboring vertebrae structure or a portion thereof.

A data set for the visualizations can be defined as a number of grid points in G dimensions, where there is V number of values in each grid point. The term "multidimensional" refers to both components, grid G and variates V, of the data sets. For data sets having a V≥1, the data set is referred to as multi-variate. As examples, a normal medical data set has G=3 and V=1, and a normal time-dependent volume has G=4 and V=1, a volume describing flow will have G=3 and V=3 (three values, since the velocity is a 3D vector). The data sets of the instant invention for medical images will typically have G and V values of G≤4 and V≤6. As known to those of skill in the art, traditional medical systems are bound by the 2D slice format used by the imaging modalities and use this base to construct higher-dimensional data.

Any document (article, web publication, patent, and patent application) identified or referenced in this document (including the background or specification) is hereby incorporated by reference as if recited in full herein.

The term "model" refers to a substantially anatomically correct 3-D model of a normal target anatomical structure of an organ, e.g., a spine model. The model can be provided as a gender specific model or made available in different model categories such as in age-range specific and/or weight/size specific ranges for both female and male versions, including pediatric, adolescent, teenage, middle age or geriatric-based models. The model(s) can be a surface model or a voxel model. The models can be anatomically correct rather than provided as geometric based models using elliptic cylinders or other non-anatomical geometric shapes. An example of a suitable voxel phantom is the XCAT, developed by Segars et al., 4D XCAT phantom for multimodality imaging research. *Medical physics,* 37(9):4902-4915, 2010. The XCAT phantom is a highly detailed phantom for both the male and the female anatomy, using non-uniform rational B-splines (NURBS) for defining the anatomy of the different organs. The phantom is typically used for simulation studies for CT, PET and SPECT. However, the XCAT was used to create a voxel model of all cervical, thoracic and lumbar vertebrae. The software accompanying the XCAT phantom allows the user to change a number of parameters, ranging from overall patient size and orientation to the inclusion of heart and/or respiratory motions.

The term "organ" refers to a group of cells performing similar functions and can include hard (bone) and/or soft tissue. Embodiments of the invention are particularly suitable for evaluating orthopedic musculoskeletal systems such as the spine and associated vertebrae. In particular embodiments, the target organ is the entire spine from T1-L5 although it is contemplated that only certain spine regions may be targeted for evaluation, e.g., T1-T12 or L1-L5, or T11-L4, for example.

The term "rapid" means for a respective patient, the patient image data set can be automatically electronically analyzed to generate computed measurements of an entire volume in less than 10 minutes, typically between about 1-5 minutes, such as 3 minutes for 12-17 vertebrae. The computed measurements can include measurements of lateral displacement, axial rotation, sagittal rotation and anterior-posterior displacement of a target organ, e.g., each vertebrae of a spine.

GUI (Graphic User Input) and other User Input (UI) controls, including GUI controls that allow touch input and touch gestures using a touch screen, are widely used and well known to those of skill in the art and will not be explained in further detail herein. GUIs and UIs can be provided with a display such as that associated with a clinician workstation to allow selection of landmark placement or other interactive input with systems and circuits that provide the spinal assessment (see, e.g., FIGS. 4B and 10).

The following description will focus primarily on automated evaluation of spinal deformity but such analysis can be used for other 3-D orthopedic bone structure evaluations. In addition, the below described voxel model can be exchanged for or used with a surface model. The below described landmarks can include additional and/or a different set of landmarks. The below described pre-processing can be exchanged for other of algorithms for detecting position and rotation of the target structure, e.g., vertebra, or for manual measurements. The below described (adaptive) image enhancement can be exchanged for or used with other techniques, such as anisotropic diffusion, non-local median filtering. The phase-based registration discussed below can be exchanged for or used with other registration techniques including other similarity measures, regularizes and optimizers.

Detailed analysis of spinal deformity can be important within orthopedic health care, in particular for assessments of idiopathic scoliosis. Embodiments of the invention propose a method capable of automatically measuring position, rotation and lateral wedging (deformation) of the vertebrae in the spine. The proposed methods differ from previously presented methods for axial vertebral rotation (AVR) measurements and are considered to be more robust to variations of the symmetry of the vertebra for measuring the rotation. Compared to stereoradiography and 3D reconstructions, the described analysis has the benefits of not requiring a dedicated imaging modality and can be used with minimal user interaction. The automated evaluation can employ a statistical analysis, which can include an eigenvector analysis of the position, rotation and deformation of the target anatomical structure, e.g., a series of vertebrae.

Embodiments of the invention provide automated estimated measurements for quantifying the degree of scoliosis and/or an automated analysis that indicate how different measures relate to each other. These automated measurements can be used to classify various sub-types of idiopathic scoliosis and to determine suitable treatments of the different sub-types.

Embodiments of the invention describe registration of a highly detailed spine model M (FIGS. 2A, 2B, 4A) to image data P (FIG. 2A, 2B, 2C) from a 3-D computed tomography (CT) data set, an MRI data set or a data set that combines both CT and MRI image data (e.g., a composite image data set). Thus, while the below description is primarily discussed for (low dose) computed tomography (CT) data using patient data sets that can be obtained from a PACS (picture archiving and communication) system, the invention is not limited thereto.

Generally stated, in some embodiments, measurements of anatomical target, such as the spine for spinal curvature, can be generated using landmarks first attached to a substantially natural 3-D model of the organ. The model is then registered to patient data. The landmarks of the model are then transferred to the patient data according to an estimated transformation for full 3D characterization. The transferred landmarks can then be utilized for measuring the position, rotation and deformation of one or more components of the organ of the patient data (e.g., each vertebra). Altering the set of landmarks selected or used, other measures describing a deformity, e.g., a spinal deformity (including other than the ones described herein), can be derived.

The analysis can optionally employ principal component analysis (PCA) and canonical correlation analysis (CCA) to determine significant correlations between the different measures.

In other embodiments, the above described process can be inverted. For example, landmarks L in a 3-D patient image P can be transferred to the model M. The reverse flow analysis may be useful to study landmark precision or registration precision. In addition or alternatively, the landmarks L can then be transferred to a second patient image data set to allow for more standardization and/or quicker placement between the two image data sets relative to manual placement.

In yet other embodiments, landmarks L from two different 3-D patient images can be transferred to the model M to measure and compare measurement differences between the two images using a common model M.

Figures 2A, 2B, 2C:
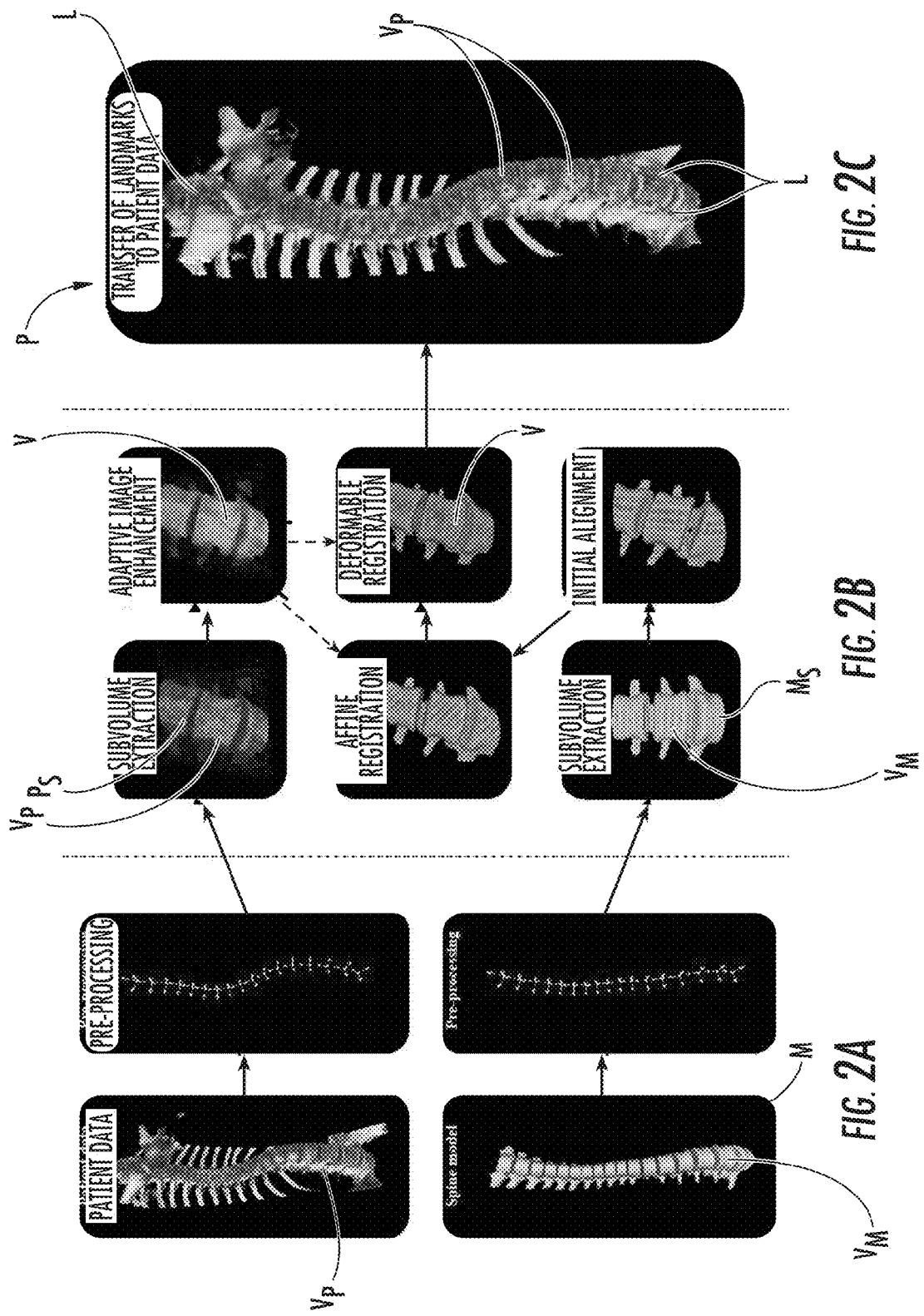
FIGS. 2A-2C are schematic illustrations of an overview of pre-processing, adaptive image enhancement, image registration and the final transfer of the landmarks to the patient data that can be used to carry out embodiments of the present invention.

Referring to FIGS. 2A-2C, an exemplary analysis of the spine is shown. The method can include pre-processing (FIG. 2A), image enhancement (FIG. 2B), and image registration and transfer of landmarks (FIG. 2C). In pre-processing, position and rotation of the discrete components of the model and patient image data are determined and/or estimated for transformation/matching of the corresponding components (e.g., corresponding vertebra). As will be discussed further below with respect to FIGS. 5A-5G, the pre-processing for position and orientation of a respective vertebra and/or disc can include extraction of the spinal canal centerline, disc detection, vertebra center point estimation and vertebra rotation estimation.

An initial pose (position and rotation) of each discrete component of the target organ (e.g., vertebra) for can be estimated. The initial pose evaluation can be applied both to the model M and to the patient data P. As shown, the rotation or position of the model may be different from the patient image data in the initial pose. Thereafter, each component of the model (e.g., each subvolume with a respective vertebra of the spine) can be registered to the corresponding component in the patient image data (e.g., to the corresponding vertebrae of the patient) and the landmarks L can be transferred to the 3-D patient image data (FIG. 2C).

In some embodiments, as shown in FIG. 2B, subvolumes Ms, Ps of the data sets containing the component to be registered and any adjacent component (e.g., vertebrae and spinal processes) can be extracted from both the model M and patient image data set P. This action is shown as "subvolume extraction" for the patient data in the top left panel in FIG. 2B and for the model in the bottom left panel of FIG. 2B. Thus, in some embodiments, before registration, the extracted subvolumes Ps can undergo 3D image enhancement in order to enhance (e.g., visually increase or resolve) image features including structures separating adjacent vertebrae. However, it is contemplated that with better resolution of the patient image data set and/or a different target organ, image enhancement may be omitted.

In some particular embodiments, as will be discussed below, adaptive image enhancement can be applied. This can improve the starting point for the subsequent registration process by improving the separation borders of adjacent vertebrae in the patient data. Adaptive image enhancement can be carried out as described in the book entitled, "Signal Processing for Computer Vision", G. Granlund and H. Knuttssson, Eds., Kluwer Academic Publishers, 1995, the contents of which are hereby incorporated by reference as if recited in full herein. However, it is also contemplated that other image enhancement techniques can be used, such as anisotropic diffusion and non-local median filtering, for example.

The registration of the model M and the patient data P can be carried out vertebra-by-vertebra V (in FIGS. 2A-2C, the patient image data vertebrae are indicated by $V_P$ and the model vertebrae are indicated by $V_M$). At least one registration method can be used to register (map) the model M to the patient data P.

As also shown in FIG. 2B, the subvolumes Ms, Ps can be registered with a two step sequential process to provide a robust registration and/or improved GPU computational performance. Thus, in some embodiments, the registration can be carried out using a first affine registration (shown in the middle left panel) to compensate for overall differences due to translation, rotation and scale, then second with a deformable registration (middle right panel). The affine registration corrects for general translation, rotation and scale differences. The deformable registration fits the vertebra model M to the patient data P. The registrations can be carried out using phase-based registrations as will be discussed further below. However, it is contemplated that other registration techniques can also be employed, such as other similarity measures (e.g., intensity, particularly for MRI patient image data), regularizers and optimizers.

The model and/or the patient data image subvolumes Ms, Ps can be rotated before the affine registration (shown as the model adjusted to the initial alignment in the bottom right panel). Estimated transformations can be composed and used to transfer the landmarks "L" of the model M to the 3D image of the patient P (FIG. 2C) for computing defined measures of position, rotation, angles and the like using a defined coordinate system and position of the landmarks L. That is, the landmarks L can be transformed according to the transformation obtained from the registration process. Then the position, rotation and deformation of the patient's vertebrae can be measured using the transferred landmarks L.

Figure 3A:
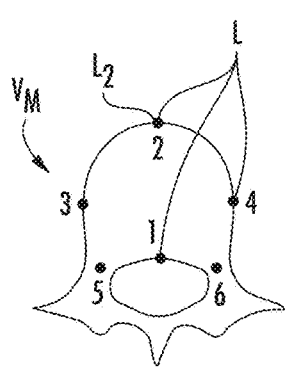
FIGS. 3A-3C illustrate an example of a portion of a 3-D model configured to allow landmarks to be positioned about defined locations thereof.
Figure 3B:
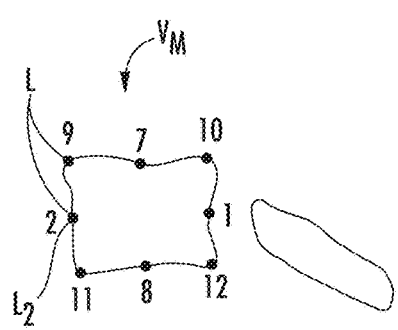
Figure 3C:
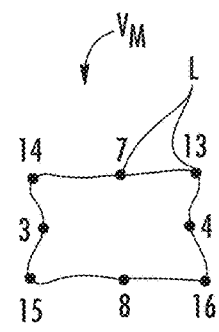

FIGS. 3A-3C illustrate that a plurality of landmarks L can be positioned about the perimeter of the model M (and, as appropriate, at certain interior spaces) in different planes, e.g., at least three orthogonal imaginary planes including axial (horizontal), sagittal (a vertical plane that intersects the axial plane), and coronal (frontal) planes that pass through the body. The analysis can also include a median (midsagittal) plane with associated landmarks L. As shown, some landmarks L can appear in more than one plane, e.g., landmark $L_2$ on the model appears in both FIGS. 3A and 3B.

FIGS. 3A-3C illustrates that the model M can be accessed as planes of respective vertebrae to place landmarks L. In some embodiments, sixteen (16) landmarks L can be used including ones placed in the (A) mid-axial, (B) mid-sagittal and (C) mid-frontal segments of each vertebra. As shown, landmarks 1-6 define the axial plane of the vertebra, landmarks 1-2 and 7-11 define the sagittal plane and landmarks 3-4, 7-8 and 13-16 define the frontal plane. It is contemplated that at least 4 landmarks L will be used for each vertebrae, with one or more in one or more planes, typically a plurality in a plurality of different planes, depending on the target measurement. However, the number of landmarks L used will depend on what is targeted for measurement and an associated definition for that measurement. While the number of landmarks used for any particular measurement or sets of measurements can vary, they typically include between about 5-30 landmarks L, such as between about 10-15 landmarks L or about 10, 11, 12, 13, 14, 15, 16, 17, 18, 19, 20, 21, 22, 23, 24, 25, 26, 27, 28, 29 and 30 landmarks L. Different numbers of landmarks L may be used for different vertebrae V (not shown).

The exemplary landmarks L shown in FIGS. 3A-3C can be electronically positioned automatically or manually placed using a GUI, for example. Landmarks L in the mid-axial, mid-sagittal and mid-frontal images of respective model vertebra are relatively easy to place, given an orthogonal multi-planar reconstruction (MPR) viewer 120 (FIG. 10), and are useful for a robust estimation of the rotation matrix R of each vertebra. The rotation matrix R of each vertebra can be determined by estimating the optimal R as minimizing $$\underset{R}{\arg\min} = \varepsilon^2(R) = \sum_{k=1}^{3} \sum_{l \in \Omega_k} [(Re_k)^T x_l]^2, \qquad \text{Equation (1)}$$

where $e_1 = [1\ 0\ 0]^T$, $e_2 = [0\ 1\ 0]^T$, $e_3 = [0\ 0\ 1]^T$ and $x_l$ is a coordinate vector corresponding to the landmarks defining the different orthogonal planes, given by the different sets $\Omega_k$. The optimal R is easily found by using a quaternion representation of R and by solving a nonlinear least-square optimization problem, e.g. using lsqnonlin in MATLAB.

The position of a respective vertebra can be estimated as the average coordinate of the landmarks L, e.g., the sixteen (16) landmarks L shown in FIGS. 3A-3C, in some embodiments.

Figure 4A:
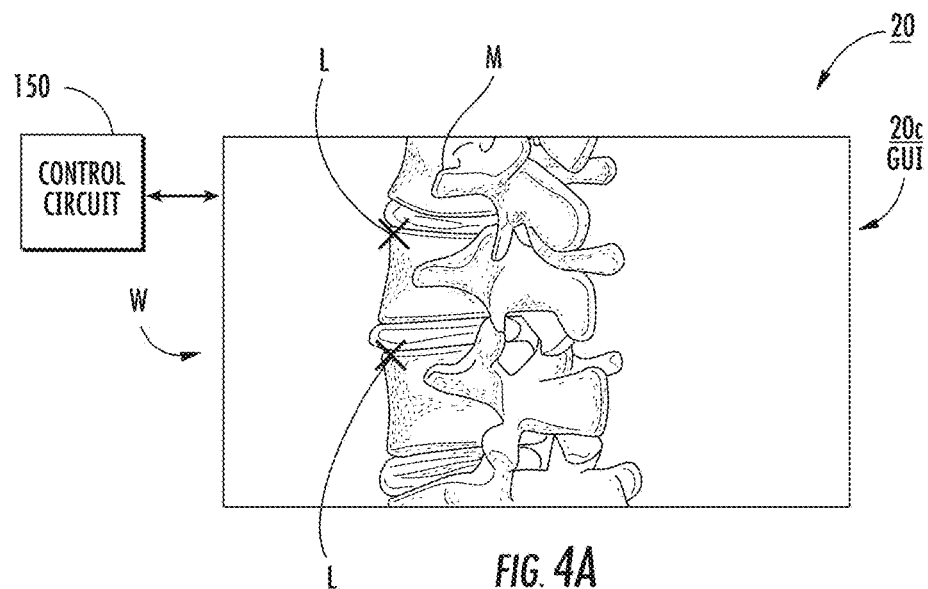
FIG. 4A is an illustration of a portion of an electronic 3-D spine model that can be used to place landmarks according to embodiments of the present invention.

As shown in FIG. 4A, the model M can be an interactive rotatable 3-D model M, e.g., a 3-D interactive rotatable model of a plurality (typically all) the vertebrae of the spine. In use, a circuit 150 with at least one processor can be configured to provide the model M to a display 20 with landmarks L in defined locations such as in the locations shown in FIGS. 3A-3C. The model M can be configured to allow a user to adjust the number (increase or decrease the number) and/or adjust a position of one or more of the predefined landmarks L. The model M can cooperate with a GUI 20c associated with the circuit 150 and display 20 that allows a user to indicate a desired landmark position (shown as marked by an "X") on the model M. The model M can be configured to separate into different components, e.g., discrete vertebrae, and/into different planes for each vertebrae and to show the different components in different planes to allow a user to see or change landmark positions.

In some embodiments, the model M can be provided without landmarks and can allow a physician to electronically tag locations for the landmarks. A template of exemplary tag locations can be selected and/or applied as a default selection.

Figure 4B:
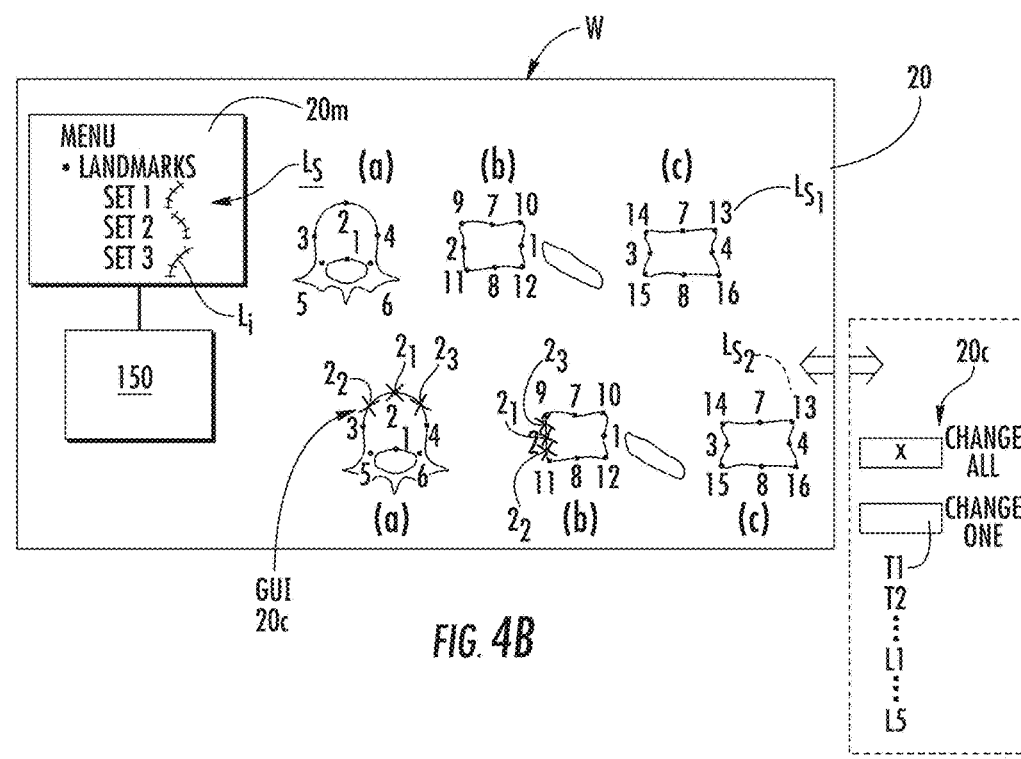
FIG. 4B is a schematic illustration of a display with a GUI and an electronic menu of defined landmarks, and selectable different vertebrae according to embodiments of the present invention.

FIG. 4B illustrates that, in some embodiments, a clinician workstation W with a display 20 or other display can be in communication with a circuit that provides an electronic menu 20m of selectable sets of predefined landmarks Ls. The different sets Ls can be presented with an icon Li that visually reflects the measurements that can be carried out using the respective set and/or may be provided with a name for a respective condition that the respective set of landmarks Ls is intended for. The different sets of landmarks Ls can be provided in an electronic library or menu for respective different medical condition evaluations to provide for more standardization of reviews and measurements, e.g., for different spinal deformities.

FIG. 4B also illustrates that if a user indicates a change in a landmark in one plane (shown as an addition of two landmarks in the mid axial plane (a), e.g., from a single landmark for position 2 to a plurality of closely spaced adjacent landmarks $2_1$, $2_2$, $2_3$), the landmark change can be automatically propagated to the other planes of a selected vertebrae (which can be itself selected from the 3-D model M) or for all vertebrae undergoing evaluation. A UI 20c can be provided to allow a user to define whether to change the landmarks in all or selected ones of the vertebrae V (shown as a selectable input of change all/change one). Other inputs can also be used to position or change a position or cancel a landmark, including "click" and "point", touch gestures and the like.

The different sets of landmarks Ls or one or more target landmarks, whether predefined or defined manually and case-specific or preference by a physician, can be selectively electronically exchanged and, upon so doing, the system/circuit 150 can generate a different set of associated measurements automatically and in a rapid manner. The different set of landmarks Ls can be defined sua sponte with respect to its location in the coordinate system or may be defined as a distance from a prior-placed and used landmark.

Pre-Processing

Figure 5G:
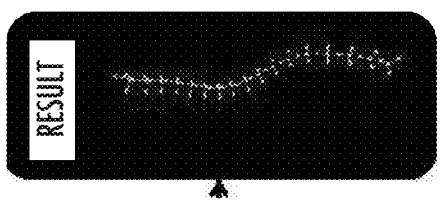
FIGS. 5A-5G are schematic illustrations of a sequence of processing actions that can be carried out to identify an estimation of an initial position and rotation of each vertebrae according to embodiments of the present invention.
Figure 5F:
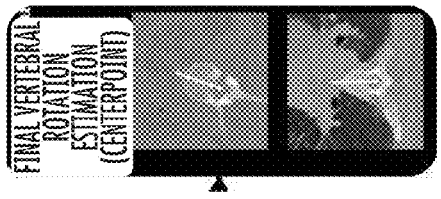
Figure 5E:
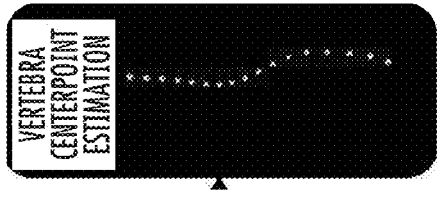
Figure 5D:
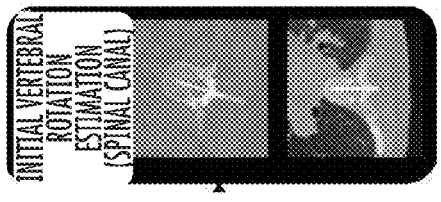
Figure 5C:
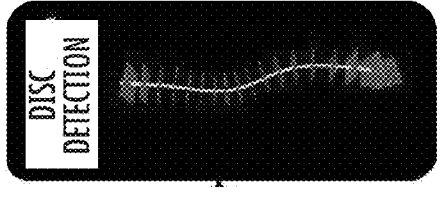
Figure 5B:
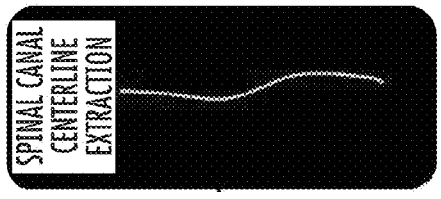
Figure 5A:
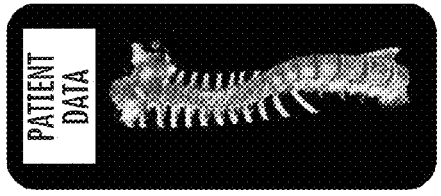

To improve the initial starting point for the registration, a pre-processing routine can be used to estimate an initial pose (position and rotation) of each vertebra as described above. Referring to FIGS. 5A-5G, the pre-processing can include: extraction of the spinal canal centerline (FIGS. 5A, 5B), disc detection (FIG. 5C), vertebra center point estimation (FIG. 5D, 5E) and vertebra rotation estimation (FIG. 5F, 5G). For additional discussion of suitable pre-processing methods, see, e.g., D. Forsberg, C. Lundström, M. Andersson, L. Vavruch, H. Tropp, and H. Knutsson. Fully automatic measurements of axial vertebral rotation for assessment of spinal deformity in idiopathic scoliosis. *Physics in Medicine and Biology*, 2013. The contents of these documents are hereby incorporated by reference as if recited in full herein. Note that although the initial starting point for the registration, as estimated from the pre-processing, can be based upon the symmetry of vertebral bodies, advantageously, the end results obtained from the subsequent registration process do not rely on symmetric vertebral bodies.

The data can optionally also be further pre-processed in order in increase the borders of adjacent vertebrae by applying a threshold at 100 Hounsfield units, to remove the influence of soft tissues during the registration process, and by applying a valley-emphasis. See, e.g., Kim, Y. and Kim, D., 2009, A fully automatic vertebra segmentation method using 3d deformable fences, *Computerized Medical Imaging and Graphics* 33(5), 343-352, the contents of which are hereby incorporated by reference as recited in full herein. A valley-emphasized image can be created by:

$$(I \cdot B)(X) = (I \oplus B) \otimes B,$$

$$V(X) = (I \cdot B) - I,$$

$$I_V(X) = (I - V),$$

where B is a 3-D window mask, which can be a 3×3×3 mm³ mask, The symbol $\oplus$ denotes dilation and the symbol $\otimes$ denotes erosion, i.e. the valley image V(X) can be constructed by subtracting the original image from its morphologically closed counterpart and the valley-emphasized image can be obtained by subtracting the valley image from the original image.

3-D Image Registration

In some embodiments, given the approximate pose of each vertebra V, the spine model M is then registered to the spine of the patient P, vertebra by vertebra, first with an affine registration followed by a deformable registration. The two types of registration can provide a more robust registration than using only a deformable registration. Also, the registration of sub-volumes has the advantage of allowing the use of GPUs for improved computational performance. This is due to the limited amount of memory available on many GPUs, causing many GPU-based implementations of registration algorithms to be limited to data sets of size 256×256×256 or smaller.

In particular embodiments, image registration can be based upon phase-difference. This is due to the fact that the local phase of a signal is relatively robust against noise, invariant to signal energy and provides sub-pixel accuracy by varying smoothly. Especially the second reason, invariance to signal energy, is relevant in the case of model-based registration, since the signal intensities of the spine model and the low-dose CT patient data (where used) may not match. Hence, the use of simple similarity measures, e.g. sum of squared intensity differences, are unlikely to perform well in this scenario. In addition, the use of phase-difference is more attractive than using more elaborate measures, e.g. mutual information, since they come with an additional computational cost.

The local phase of an image can be estimated using oriented quadrature filters, see, e.g., G. Granlund and H. Knutsson, editors. *Signal Processing for Computer Vision*. Kluwer Academic Publishers, 1995.

The initial affine registration can be carried out by employing the algorithm described by M. Hemmendorff, M. Andersson, T. Kronander, and H. Knutsson. Phase-based multidimensional volume registration. *IEEE Transactions on Medical Imaging*, 21(12):1536-1543, 2002, and implemented using the compute unified device architecture (CUDA) by A. Eklund, M. Andersson, and H. Knutsson. Phase based volume registration using CUDA. In *Acoustics Speech and Signal Processing* (ICASSP), 2010 IEEE International Conference on, pages 658-661. IEEE, 2010. The final deformable registration can be carried out using a registration algorithm known as "the Morphon". This method was introduced by H. Knutsson and M. Andersson. Morphons: Segmentation using elastic canvas and paint on priors. In *Image Processing*, 2005. ICIP 2005. *IEEE International Conference on*, volume 2, pages II-1226-9. IEEE, 2005 and described in CUDA by D. Forsberg, A. Eklund, M. Andersson, and H. Knutsson. Phase-based non-rigid 3D image registration—from minutes to seconds using CUDA. In *HP-MICCAI/MICCAI-DCI* 2011. The contents of the references in this paragraph are hereby incorporated by reference as if recited in full herein.

Quadrature Filters and Local Phase

Quadrature filters are complex valued filters combining detection of even and odd rank 1 structures, where the real filter part is sensitive to even structures and the imaginary part is sensitive to odd structures. The phase of the filter response determines the structural content (odd or even) and the magnitude provides a certainty of this estimate. In some embodiments, log-normal quadrature filters F, which in the Fourier domain, can be expressed as a combination of a spherical separable function R and a directional function D.

$$F = R(\|u\|)D(u) \quad \text{Equation (2)}$$

$$R(\|u\|) = e^{-C\ln^2\left(\frac{\|u\|}{u_0}\right)} \quad \text{Equation (3)}$$

$$C = \frac{4}{B^2 \ln(2)} \quad \text{Equation (4)}$$

Here u denotes the frequency, $u_0$ the center frequency of the quadrature filter and B the relative bandwidth in octaves. Since the phase concept is only valid in a defined direction, different directional functions are needed. Hence, set D to $$D_k(u) = \begin{cases} (u^T \hat{n}_k)^2 & u^T \hat{n}_k > 0 \\ 0 & \text{otherwise,} \end{cases} \quad \text{Equation (5)}$$

where $\hat{n}_k$ is the directional vector for filter $F_k$. Hence, the local phase $\phi_k$ in the direction $\hat{n}_k$ is given by $\phi_k(x) = \arg[q_k(x)]$ where $q_k(x) = (I * f_k)(x)$, I is the image and * denotes convolution.

Adaptive Image Enhancement

Before the registration process, a step of adaptive image enhancement can be carried out. This action may be particularly suitable where the analyzed data is somewhat noisy (e.g., low-dose CT data) so that the structures separating adjacent vertebra may not always be well-defined. This can cause the registration to sometimes fail, due to being unable to differentiate between adjacent endplates and processes of the vertebrae. As adaptive image enhancement, an adaptive filtering algorithm can be used. See, e.g., G. Granlund and H. Knutsson, editors. *Signal Processing for Computer Vision*. Kluwer Academic Publishers, 1995, the contents of which are hereby incorporated by reference as if recited in full herein.

1. Filter the image volume I with a set of directional quadrature filters $F_k$.

$$q_k = I * f_k \quad \text{Equation (6)}$$

2. Construct the local structure tensor T $$T = \Sigma_k q_k M_k, \quad \text{Equation (7)}$$

where $M_k$ is the dual tensor of $\hat{n}_k \hat{n}_k^T$, defined as $$M_k = \frac{5}{4} \hat{n}_k \hat{n}_k^T - \frac{1}{4} I. \quad \text{Equation (8)}$$

Note that Equation (9) is only valid if $\hat{n}_k$ refers to the vectors pointing to the vertices of a hemi-icosahedron as described in Granlund et al., supra.

3. Construct a control tensor C based upon the eigenvectors and the mapped eigenvalues $\lambda_n$ of T.

$$C = \Sigma_{n=1}^N \lambda_n \hat{e}_n \hat{e}_n^T \quad \text{Equation (9)}$$

4. Let the control tensor steer the adaptive filter $F_{adap}$ used for image enhancement according to:

$$F_{adap}(u,C) = F_{lp}(\rho) + \alpha_{hp} F_{hp}(u,C) \quad \text{Equation (10)}$$

$$F_{hp}(u,C) = \Sigma_k s_k F_{hp_k}(u) \quad \text{Equation (11)}$$

$$s_k = \langle C, M_k \rangle \quad \text{Equation (12)}$$

Adaptive image enhancement can also be implemented in CUDA for improved computational performance.

Affine Registration

The affine phase-based registration can be based upon the traditional optical flow Equation 13, $$\nabla I^T v - \Delta I = 0, \quad \text{Equation (13)}$$

but replaced with its phase-based counterpart per Equation 15, $$\nabla \phi^T v - \Delta \phi = 0, \quad \text{Equation (14)}$$

where $$\Delta \phi = \phi_1 - \phi_2 = \arg(q_1 q_2^*) \quad \text{Equation (15)}$$

$$q_1 = I_1 * f, \quad \text{Equation (16)}$$

$$q_2 = I_2 * f, \quad \text{Equation (17)}$$

f is the quadrature filter F in the spatial domain, and $I_1$ and $I_2$ are the two images to be registered. The displacement v is estimated by utilizing a parameterization of the displacement field per Equations 18-24.

$$v(x) = \begin{bmatrix} p_1 & p_2 & p_3 \\ p_4 & p_5 & p_6 \\ p_7 & p_8 & p_9 \end{bmatrix} \begin{bmatrix} x \\ y \\ z \end{bmatrix} + \begin{bmatrix} p_{10} \\ p_{11} \\ p_{12} \end{bmatrix} = B(x)p, \quad \text{Equation (18)}$$

$$B(x) = \begin{bmatrix} x & y & z & 0 & 0 & 0 & 0 & 0 & 0 & 1 & 0 & 0 \\ 0 & 0 & 0 & x & y & z & 0 & 0 & 0 & 0 & 1 & 0 \\ 0 & 0 & 0 & 0 & 0 & 0 & x & y & z & 0 & 0 & 1 \end{bmatrix}, \quad \text{Equation (19)}$$

$$p = [p_1, p_2, p_3, p_4, p_5, p_6, p_7, p_8, p_9, p_{10}, p_{11}, p_{12}]^T, \quad \text{Equation (20)}$$

and defining an $L_2$ norm, $$\varepsilon^2 = \frac{1}{2} \sum_k \sum_i c_{ik} [\nabla \varphi_k(x_i)^T B(x_i)p - \Delta \varphi_k(x_i)]^2, \quad \text{Equation (21)}$$

where $$c_k = \sqrt{|q_{1k} q_{2k}|} \cos^2\left(\frac{\Delta \varphi_k}{2}\right). \quad \text{Equation (22)}$$

Differentiating $\varepsilon^2$ with respect to p and setting to 0 gives $$\underbrace{\sum_k \sum_i c_{ik} B_i^T \nabla \varphi_{ik} \nabla \varphi_{ik}^T B_i p}_{A} = \underbrace{\sum_k \sum_i c_{ik} B_i^T \nabla \varphi_{ik} \Delta \varphi_{ik}}_{h} \quad \text{Equation (23)}$$

with the solution $$p = A^{-1} h. \quad \text{Equation (24)}$$

Variables in (23) with the subscript i corresponds to the values at the different spatial locations $x_i$, e.g. $B_i = B(x_i)$. The described algorithm is easily applied in an iterative multi-resolution framework by accumulating p, setting $\tilde{I}_2(x) = I_2((x) + v(x))$ and replacing $I_2$ with $\tilde{I}_2$ in Equation (17).

Deformable Registration

The deformable phase-based registration algorithm (the Morphon) can be embedded into a generic registration framework for non-parametric image registration with decoupled similarity optimization and regularization as follows (using the same notation as in the previous section). See, e.g., G. Janssens, L. Jacques, J. O. de Xivry, X. Geets, and B. Macq. Diffeomorphic registration of images with variable contrast enhancement. *Journal of Biomedical Imaging*, page 16, 2011, the contents of which are hereby incorporated by reference as if recited in full herein.

Let $d_u$ denote the update field and d the total displacement field. Define a pixel-wise least-square problem as $$\epsilon^2 = \Sigma_k [c_k T(d_k \hat{n}_k - d_u)]^2, \quad \text{Equation (25)}$$

where T is the local structure tensor, $d_k$ the displacement in direction k associated with the phase-difference according to $d_k = \Delta \phi_k / u_0$ and $c_k$ as previously defined. Differentiating and setting the derivatives to 0 will provide a linear equation system, which is easily solved, providing a pixel-wise update field.

$$A d_u = b \Leftrightarrow d_u = A^{-1} b \quad \text{Equation (26)}$$

For fluid-like registration, regularize $d_u$ with a Gaussian kernel $$d_u = d_u * g_{fluid} \quad \text{Equation (27)}$$

and then accumulate the update field to the total displacement field.

$$d = d + d_u. \quad \text{Equation (28)}$$

Finally, if diffusion-like registration, regularize d with a Gaussian kernel.

$$d = d * g_{diffusion}. \quad \text{Equation (29)}$$

In some embodiments, the estimated transformation can be used to transfer the landmarks L of the model M to the patient data P. Therefore, it can be important to have an effective way of computing the inverse transform. Since the Morphon is embedded into this generic registration framework, which is similar to the traditional framework of the demons registration algorithm, the approach described in is applicable for implementing a symmetric registration based upon diffeomorphic registration in the log-domain. This is achieved using stationary velocity fields for encoding the spatial transformation. Apart from providing a symmetric registration, this approach also has the benefit of providing a relatively simple method for computing the inverse transformation. See, e.g., J. P. Thirion. Image matching as a diffusion process: an analogy with Maxwell's demons. *Medical image analysis*, 2(3):243-260, 1998 (the demons registration algorithm); and T. Vercauteren, X. Pennec, A. Perchant, and N. Ayache. Symmetric log-domain diffeomorphic registration: A demons-based approach. In D. Metaxas, L. Axel, G. Fichtinger, and G. Szekely, editors, *Medical Image Computing and Computer-Assisted Intervention MICCAI 2008*, volume 5241 of *Lecture Notes in Computer Science*, pages 754-761. Springer Berlin Heidelberg, 2008 (diffeomorphic registration), the contents of which are hereby incorporated by reference as if recited in full herein.

Registration Discussion

In order to evaluate the proposed method, four CT data sets containing the spines from patients suffering from scoliosis where retrospectively gathered from the picture archiving and communication system at the local hospital, all data sets included vertebrae T1-L5, i.e., 17 vertebrae each and 68 vertebrae in total. The images were captured as a part of the standard routine for pre-operational planning and a specific low-dose protocol was in use, in order to minimize the delivered radiation dose (M. K. Kalra, P. Quick, S. Singh, M. Sandborg, and A. Persson. Whole spine CT for evaluation of scoliosis in children: feasibility of sub-millisievert scanning protocol. *Acta Radiologica*, 54(2):226-230, 2013). Before processing, the image data was resampled to an isotropic resolution of 1×1×1 mm3 using tri-linear interpolation in order to allow the usage of quadrature filters with isotropic resolution. Three different measures were employed to evaluate the proposed method, two measures evaluating the registration accuracy and one measure for evaluating the actual estimates derived from the transferred landmarks. As can be noted, the emphasis in the evaluation is on registration accuracy, which is natural, since the method is based on image registration. For the sake of evaluating the registration accuracy, each vertebra (in all four patients) were marked with the corresponding landmarks as defined for the model in FIGS. 3A-3C. In addition, each vertebra was manually segmented. Thereafter, each dataset was processed according to the proposed method. The manually placed landmarks and the transferred landmarks were used to assess the registration accuracy by employing target registration error (TRE), i.e. the distance between corresponding landmarks. The manual hand segmentations were compared with the segmentations obtained form the deformed models using a point-to-surface error (PSE). The PSE is defined as the smallest distance between a node on the deformed model and the closest surface of the manual segmentation. The meshes defining the vertebrae of the deformed model and the handsegmented vertebrae were acquired from their corresponding binary volumes using iso2mesh (Fang, Q. and Boas, D. A.: 2009, Tetrahedral mesh generation from volumetric binary and grayscale images, *Biomedical Imaging: From Nano to Macro*, 2009. ISBI '09. IEEE International Symposium on, IEEE, pp. 1142-1145). The surface of each vertebra was approximated using 1500-3500 nodes, where the number of nodes depended on the actual size of the vertebra.

To evaluate the estimated measures from the transferred landmarks, the AVR for all vertebrae were manually measured by three observers employing the method of Aaro and Dahlborn. See, S. Aaro and M. Dahlborn. Estimation of vertebral rotation and the spinal and rib cage deformity in scoliosis by computer tomography. *Spine*, 6(5):460-467, 1981. This is done by measuring the angle between a straight line through the dorsal central aspect of the vertebral foramen and the centrepoint of the vertebral body, and a line parallel to the sagittal image plane of the image volume. To compensate for the possible tilt of the vertebral body in the sagittal and/or the frontal plane, the image data was resampled using curved planar reformation. The resampling was done orthogonal to a curve running through the centrepoints of the vertebral bodies, centrepoints defined by each observer. The average AVR measurement from the three observers for each vertebrae was considered as the ground truth AVR. Corresponding AVR measurements are easily derived from the estimate rotation matrices R of each vertebra. The AVR is estimated as the angle between the normal vector of the frontal plane of the vertebra and the normal vector of the frontal plane of the image volume, projected onto the axial plane of the vertebra. Mean and standard deviation of the difference in AVR measurements (AVR) between manual and automatic measurements, were used to evaluate the AVR measurements. All three measures were estimated for using only affine registration (A) and for using affine registration and deformable registration (A+D). Results from the evaluation are given in Table 1.

TABLE 1

COMPARATIVE MEASUREMENTS

|  | TRE [mm] | PSE [mm] | ΔAVR [°] |
|---|---|---|---|
| A[a] | 3.0 ± 1.8 | 1.3 ± 1.0 | 0.5 ± 3.3 |
| A + D[b] | 2.3 ± 1.7 | 0.9 ± 1.9 | 0.1 ± 3.1 |

[a]Affine registration
[b]Deformable registration

Data Analysis Scheme

To show the potential that the automated analysis has for aiding clinicians in their assessment and understanding of spinal deformities, such as idiopathic scoliosis, measurements obtained with the proposed method were analyzed to determine which measures, describing spinal deformity, that appears to carry the most information.

Image Data

Image data from 15 female patients were retrospectively gathered and extracted from the local picture archiving and communications system, where the only criteria for inclusion was idiopathic scoliosis and having CT data with a resolution higher than 1×1×1 mm³. Note that the employed patients in this part is separate from those used in the evaluation in the Image Registration Evaluation above. The requirement on the resolution was needed in order to be able to distinguish adjacent vertebrae. The patients had an average age of 16.2±3.5 years at the time of their examinations and an average Cobb angle of 58.5°±9.0 (standing position). Further information regarding the patients can be found in Table 2.

The images were captured as a part of the standard routine for pre-operational planning. Note that for patients of similar age as included in a retrospective study, it is often questionable whether a CT scan is appropriate or not, due to the exposure to radiation. However, some hospitals have a protocol in place for acquiring low-dose CT examinations with maintained image quality, targeted towards examinations of the spine. With the use of this protocol, the radiation dose is approximately 0.4 mSv. More on this can be found in the recent work by Kalra et al. See, e.g., M. K. Kalra, P. Quick, S. Singh, M. Sandborg, and A. Persson. Whole spine CT for evaluation of scoliosis in children: feasibility of sub-millisievert scanning protocol. *Acta Radiologica*, 54(2):226-230, 2013.

The image data was anonymized before being exported by clinical staff. Before processing all data sets were resampled to an isotropic resolution of 1×1×1 mm³ using tri-linear interpolation.

Curvature Measures

Each data set was processed with the earlier described algorithm, resulting in 16 transferred landmarks per vertebrae. For each vertebra, the following measures were estimated based upon the transferred landmarks:

[x, y, z]—position;
[$\theta_X$, $\theta_Y$, $\theta_Z$]—rotation; and
ξ—local deformity (lateral vertebral wedging).

The position was estimated as the average coordinate of the transferred landmarks and the rotation angles were computed as the Euler angles (using a fixed world frame) of the rotation matrix R estimated according to S. Aaro and M. Dahlborn. Estimation of vertebral rotation and the spinal and rib cage deformity in scoliosis by computer tomography. *Spine*, 6(5):460-467, 1981, the contents of which are hereby incorporated by reference as if recited in full herein.

Figure 6:
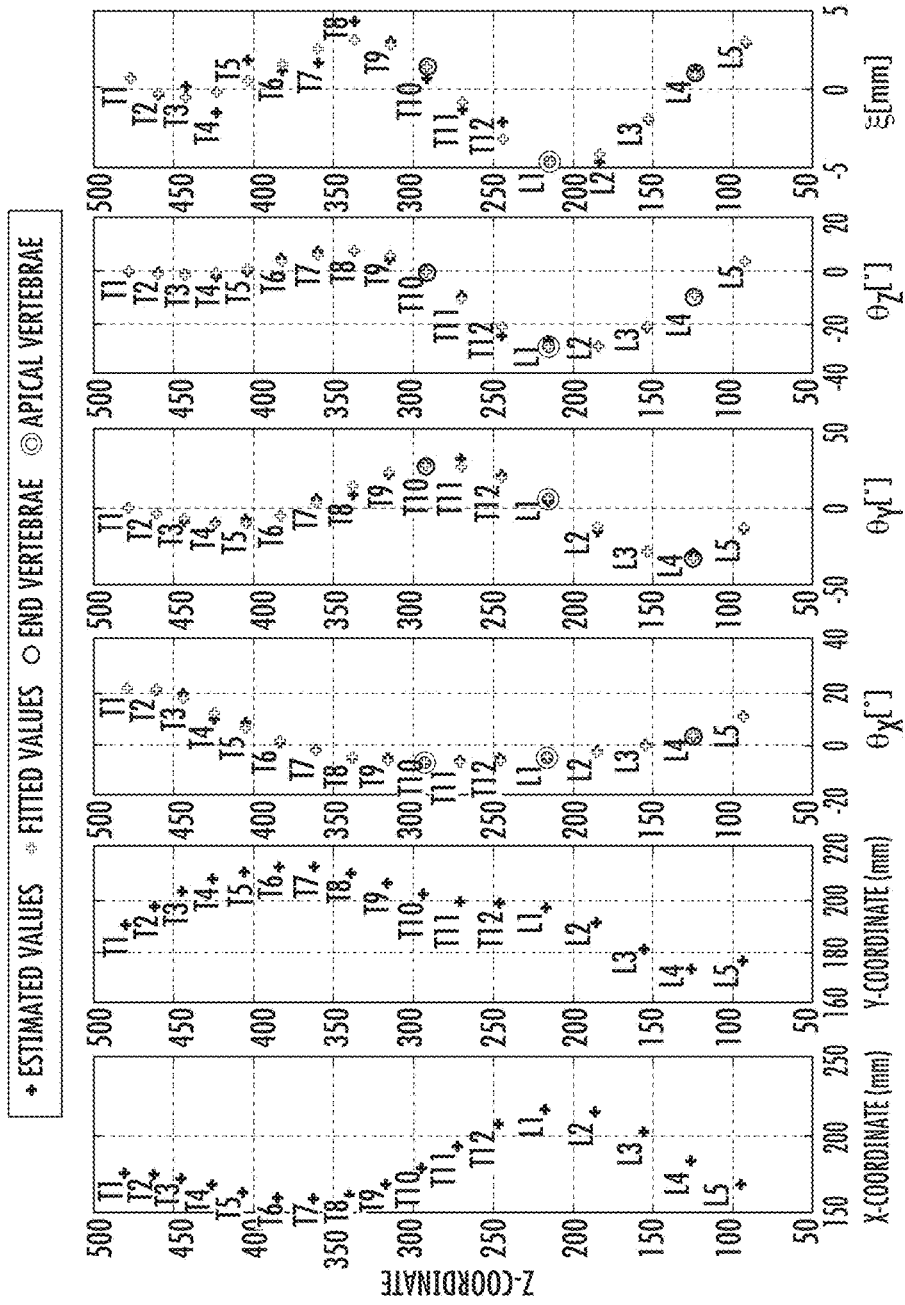
FIG. 6 illustrates graphs that show calculated measurements from patient analyzed data sets according to embodiments of the present invention. According to some optional features, the primary curvature with its end vertebrae and apical vertebra are shown as marked, where the end vertebrae are given by the vertebrae with maximal/minimal frontal rotation $\theta_y$.

Note that the order of the rotational angles, $R=R_Z(\theta_Z)R_Y(\theta_Y)R_X(\theta_X)$, is important: $\theta_Z$ corresponds to axial vertebral rotation, $\theta_Y$ to frontal rotation and $\theta_X$ to sagittal rotation. The local deformity ξ was defined as the lateral vertebral height difference of the vertebral height measurements, obtained from the distances between landmarks 14-15 and 13-16, i.e. lateral vertebral wedging. In some embodiments, the standard DICOM patient coordinate system for defining the orientation of [x, y, z], i.e. x increases from right to left, y from anterior to posterior and z from inferior to superior. To compensate for some irregularities in the obtained measurements, the rotation and deformation measures were smoothed by fitting a cubic B-spline with four knots. FIG. 6 shows graphs of the estimated measurements (two left panels) along with the fitted values of one of the analyzed data sets.

FIG. 6 shows the estimated measurements from one of the analyzed data sets. In this case, the primary curvature with its end vertebrae and apical vertebra have also been marked (with circles), where the end vertebrae are given by the vertebrae with maximal/minimal frontal rotation $\theta_Y$.

TABLE 2

PATIENT DATA

| Patient | Age | Cobb angle [°] | Lenke type |
|---|---|---|---|
| 1 | 26 | 51.7/32.4 | 5c |
| 2 | 20 | 54.2/46.9 | 1a |
| 3 | 20 | 44.5/39.2 | 6c |
| 4 | 19 | 54.2/40.9 | 3b |
| 5 | 16 | 62.8/47.6 | 1a |
| 6 | 15 | 61.7/48.0 | 3c |
| 7 | 15 | 67.5/56.0 | 2c |
| 8 | 16 | 47.4/36.8 | 6c |
| 9 | 15 | 50.4/34.7 | 6c |
| 10 | 14 | 65.5/63.6 | 3c |
| 11 | 14 | 54.5/41.6 | 3c |
| 12 | 15 | 60.7/56.1 | 6c |
| 13 | 14 | 66.3/62.3 | 3b |
| 14 | 12 | 80.5/74.1 | 4c |
| 15 | 12 | 55.3/48.1 | 4c |

The different Cobb angles were measured in standing/supine position.

PCA and CCA

Principal component analysis (PCA) and canonical correlation analysis (CCA) are two standard techniques for unsupervised learning. A brief review to both techniques is provided below.

Let X denote the data matrix $X=[x_1 \ x_2 \ \ldots \ x_n]$ and $x_i=[x_{i1} \ x_2 \ \ldots \ x_p]^T$, i.e. X contains n measurements of p variables. Define similarly the data matrix Y. For PCA, a linear transform W is estimated such that the variance of $Z=W^TX$ is maximized and where the components $w_i$ of W are orthogonal, i.e. the components of Z will be uncorrelated. In CCA, two linear transforms, $W_x$ and $W_y$, are estimated such that the correlation $\rho_i$ between the reduced variables (canonical variates) of $W_{x,i}^TX$ and $W_{y,i}^TY$, have been maximized. Note that for CCA, the data matrices X and Y do not have to have the same number of variables, but that the number of canonical variates will correspond to the smallest number of variables provided by either X or Y.

An interesting aspect of CCA is its relation with mutual information (MI). As shown by J. Kay, the mutual information between X and Y can be estimated as the sum of the mutual information of the reduced variables, given that their statistical dependence is limited to correlation. See, e.g., J. Kay. Feature discovery under contextual supervision using mutual information. In *Neural Networks, 1992. IJCNN., International Joint Conference on*, volume 4, pages 79-84.

IEEE, 1992, the contents of which are hereby incorporated by reference as if recited in full herein.

For Gaussian variables, this relation is given as $$MI(X, Y) = \frac{1}{2}\sum_i \log\left(\frac{1}{(1-\rho_i^2)}\right).$$  Equation (30)

This measure will be employed in the subsequent analysis for quantifying the dependence between different measures.

Curvature Analysis of the Entire Spine

In the data analysis, the curves of each measure, apart from the z-coordinates, for the entire spine were analyzed. Hence, the actual estimated z-coordinates were not analyzed. Rather, the vertebrae indexes defined the order of the measurements per curve, i.e. each measure was embedded into a 17 dimensional space. Each curve ensemble was then processed with PCA to find its principal components. After the PCA, CCA was applied on the measures projected onto the subspace spanned by the largest PCA eigenvectors of each measure, corresponding to 99% of the variance of the respective measures. The CCA was applied to analyze the dependence between the different measures.

CCA was not applied directly on the estimated measures due to the large number of variables (17 vertebrae) compared to the low number of observations (15 patients), which will cause singularities in the computations of the CCA, so a dimension reduction was called for. Second, using CCA directly is likely to generate an over fitting, i.e. it can find correlations related more to noise in the signal than to the relevant variations in the signal, hence smoothing or regularization was called for. Both of these requirements can be met by performing a PCA and projecting the signal onto the subspace spanned by the eigenvectors.

Results

Figure 7:
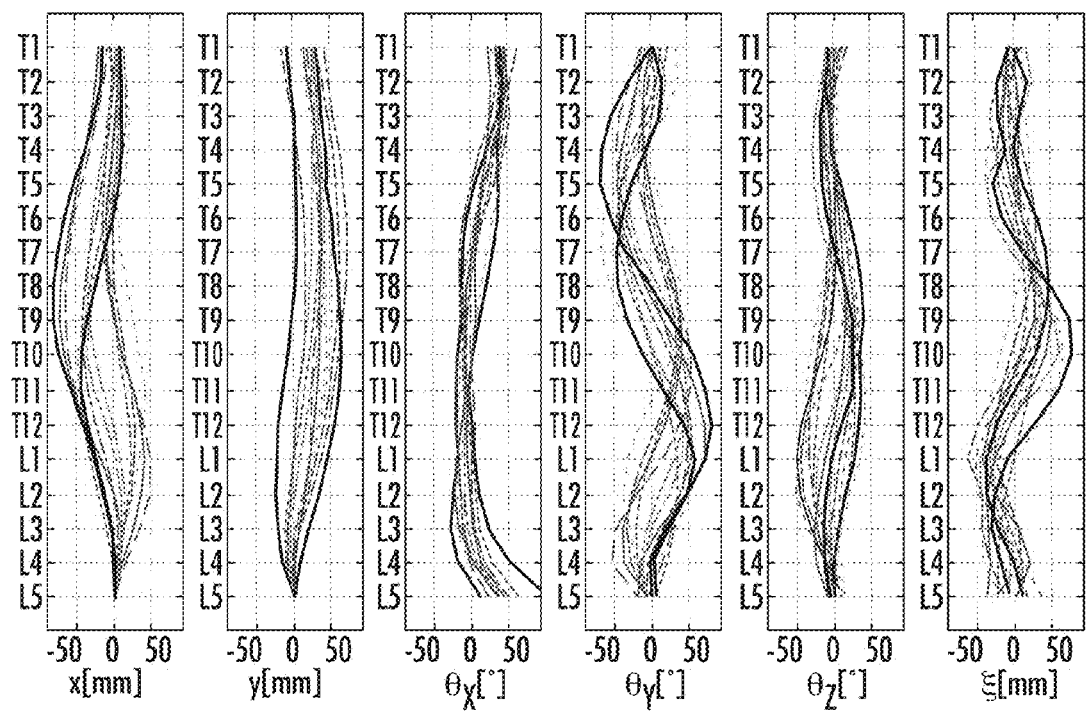
FIG. 7 illustrates graphs corresponding to those shown in FIG. 6 but illustrating all measurements of all patients of analyzed data according to embodiments of the present invention.

In the conducted experiment, PCA was applied to each estimated measure, apart from the z-coordinates, over all patients, followed by a CCA on each pair-wise combination of the measures. FIG. 7 depicts the measurements over all measures and patients. From the estimated eigenvalues, the eigenvectors corresponding to at least 99% of the variance in the data were extracted. This meant for instance that the variance in x-coordinates could be reduced to three eigenvectors, whereas the curves of $\theta_x$ required six eigenvectors, depicted in FIG. 8. The CCA was applied onto every pair-wise combination of the measures, where the measures were projected onto the subspace spanned by the eigenvectors corresponding to 99% of the variance. This was done to find dependencies between the different measures. Table 3 provides the obtained canonical correlations of all pair-wise CCAs along with corresponding MI estimates. Note the difference in number of canonical correlation coefficients between the different pair-wise comparisons. The number of canonical correlation coefficients corresponds to the smallest number of eigenvectors, required to account for 99% of the variance in the different measures.

The results show that the strongest linear dependence exists between the x-coordinates and $\theta_Y$. A somewhat weaker but still obvious dependence is found between the y-coordinates and $\theta_X$, between $\theta_Y$ and $\theta_Z$, and between $\theta_Y$ and $\xi$. Or, as expressed in anatomical terms, the lateral displacement of the vertebral body is highly correlated with the frontal rotation of the same. In addition, sagittal rotation and anterior-posterior displacement of the vertebrae is highly correlated. Somewhat weaker but still strong correlations are also found between frontal rotation and both axial vertebral rotation and vertebral deformation.

Figure 8:
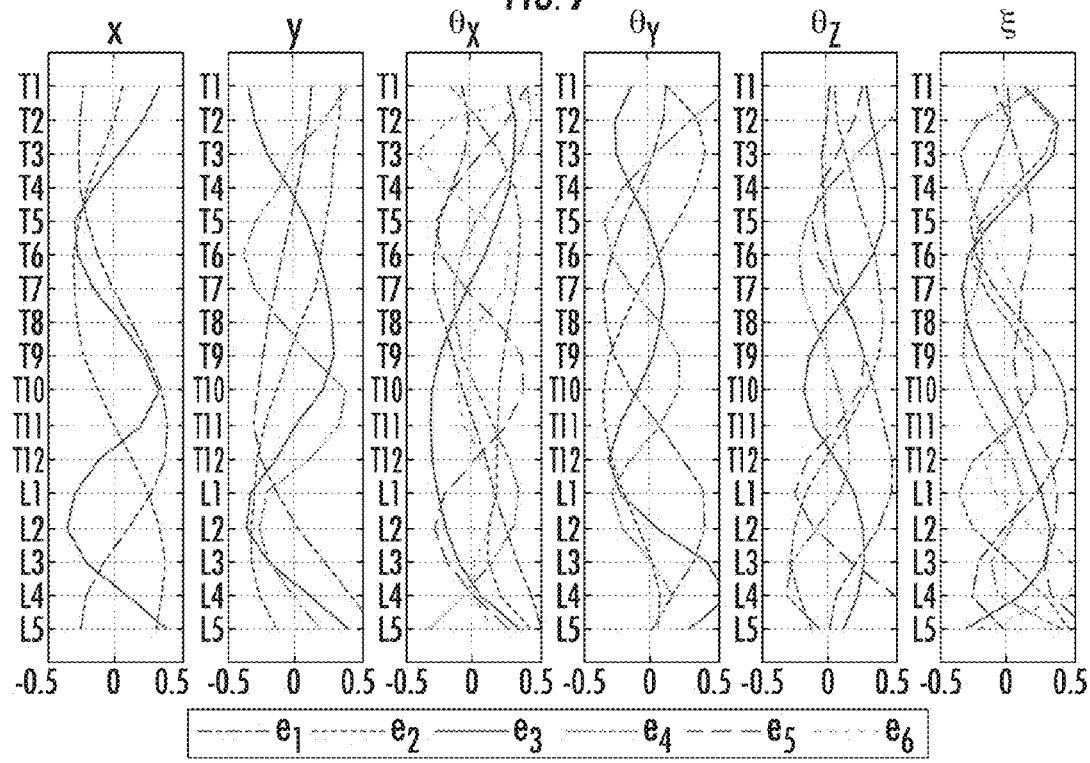
FIG. 8 are graphs of eigenvectors belonging to the largest eigenvector values as estimated from PCA with only the number of eigenvectors required to account for at least 99% variance in the data included according to embodiments of the present invention.

FIG. 8 shows the Eigenvectors belonging to the largest eigenvalues as estimated from the PCA with only the number of eigenvectors required to account for at least 99% of the variance in the data have been included.

TABLE 3

CANONICAL CORRELATIONS AND MUTUAL INFORMATION AS OBTAINED FROM THE PAIR-WISE CCA, SORTED ACCORDING TO ESTIMATED MI.

| | $\rho_1$ | $\rho_2$ | $\rho_3$ | $\rho_4$ | $\rho_5$ | $\rho_6$ | MI |
|---|---|---|---|---|---|---|---|
| x-$\theta_Y$ | 1.00 | 0.98 | 0.96 | | | | 7.83 |
| y-$\theta_X$ | 0.99 | 0.98 | 0.94 | 0.87 | | | 7.64 |
| $\theta_Y$-$\theta_Z$ | 1.00 | 0.98 | 0.93 | 0.20 | | | 7.15 |
| $\theta_Y$-$\xi$ | 0.99 | 0.96 | 0.89 | 0.80 | | | 7.01 |
| x-$\theta_Z$ | 0.99 | 0.99 | 0.89 | | | | 6.87 |
| $\theta_Z$-$\xi$ | 1.00 | 0.94 | 0.85 | 0.68 | 0.20 | | 6.33 |
| $\theta_X$-$\xi$ | 0.98 | 0.90 | 0.81 | 0.72 | 0.39 | 0.10 | 4.87 |
| x-$\xi$ | 0.99 | 0.92 | 0.84 | | | | 4.86 |
| $\theta_X$-$\theta_Y$ | 0.97 | 0.88 | 0.72 | 0.54 | | | 3.97 |
| $\theta_X$-$\theta_Z$ | 0.94 | 0.90 | 0.73 | 0.55 | 0.47 | | 3.70 |
| y-$\xi$ | 0.93 | 0.80 | 0.66 | 0.53 | | | 2.80 |
| x-$\theta_X$ | 0.94 | 0.80 | 0.54 | | | | 2.51 |
| y-$\theta_Z$ | 0.84 | 0.83 | 0.57 | 0.21 | | | 2.07 |
| y-$\theta_Y$ | 0.85 | 0.73 | 0.68 | 0.03 | | | 1.91 |
| x-y | 0.74 | 0.68 | 0.15 | | | | 1.03 |

As discussed above, embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 9:
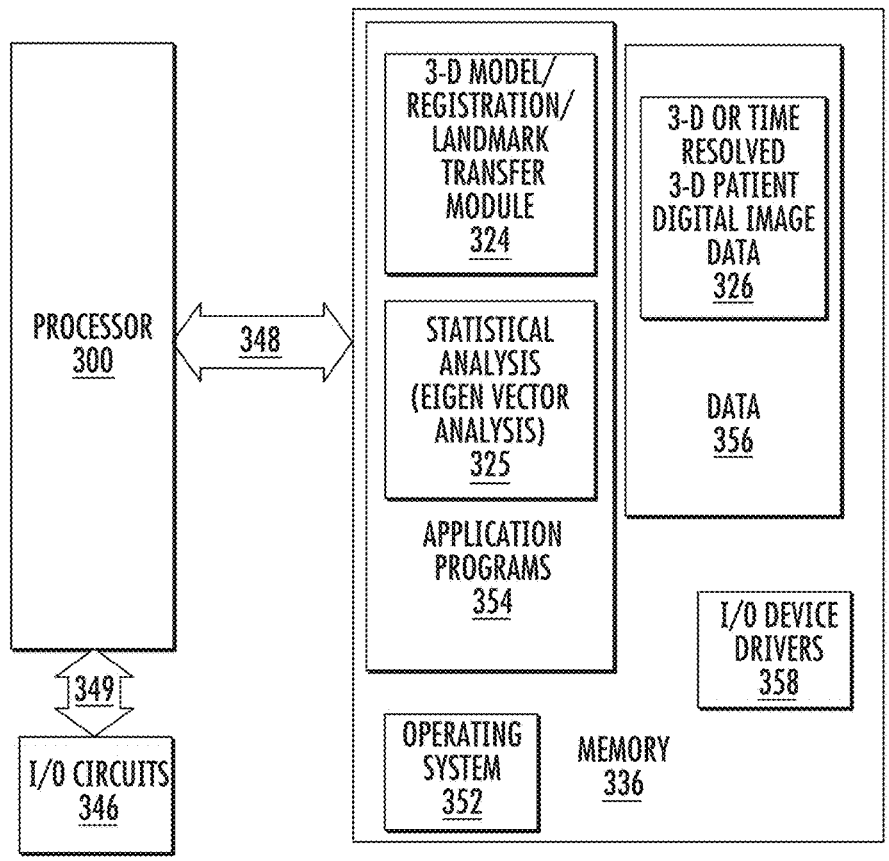
FIG. 9 is a block diagram of a data processing system according to embodiments of the present invention.

As illustrated in FIG. 9, embodiments of the invention may be configured as a data processing system 116, which can be used to carry out or direct operations of the rendering, and can include a processor circuit 300, a memory 336 and input/output circuits 346. The data processing system may be incorporated in, for example, one or more of a personal computer, workstation W (FIGS. 4A and 10), server, router or the like. The system 116 can reside on one machine or be distributed over a plurality of machines. The processor 300 communicates with the memory 336 via an address/data bus 348 and communicates with the input/output circuits 346 via an address/data bus 349. The input/output circuits 346 can be used to transfer information between the memory (memory and/or storage media) 336 and another computer system or a network using, for example, an Internet protocol (IP) connection. These components may be conventional components such as those used in many conventional data processing systems, which may be configured to operate as described herein.

In particular, the processor 300 can be commercially available or custom microprocessor, microcontroller, digital signal processor or the like. The memory 336 may include any memory devices and/or storage media containing the software and data used to implement the functionality circuits or modules used in accordance with embodiments of the present invention. The memory 336 can include, but is not limited to, the following types of devices: ROM, PROM, EPROM, EEPROM, flash memory, SRAM, DRAM and magnetic disk. In some embodiments of the present invention, the memory 336 may be a content addressable memory (CAM).

As further illustrated in FIG. 9, the memory (and/or storage media) 336 may include several categories of software and data used in the data processing system: an operating system 352; application programs 354; input/output device drivers 358; and data 356. As will be appreciated by those of skill in the art, the operating system 352 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 358 typically include software routines accessed through the operating system 352 by the application programs 354 to communicate with devices such as the input/output circuits 346 and certain memory 336 components. The application programs 354 are illustrative of the programs that implement the various features of the circuits and modules according to some embodiments of the present invention. Finally, the data 356 represents the static and dynamic data used by the application programs 354 the operating system 352 the input/output device drivers 358 and other software programs that may reside in the memory 336.

The data 356 may include (near real time or archived or stored) digital image data sets 326 that provides stacks of image data including meta data regarding, for example, voxel size (DICOM data to correlate the image data to respective patients). As further illustrated in FIG. 9, according to some embodiments of the present invention application programs 354 include a 3-D Model, Registration and Landmark Transfer Module 324 and optionally a Statistical Analysis (e.g., Eigenvector analysis) Module 325. The application program 354 may be located in a local server (or processor) and/or database or a remote server (or processor) and/or database, or combinations of local and remote databases and/or servers.

While the present invention is illustrated with reference to the application programs 354, and Modules 324, 325 in FIG. 9, as will be appreciated by those of skill in the art, other configurations fall within the scope of the present invention. For example, rather than being application programs 354 these circuits and modules may also be incorporated into the operating system 352 or other such logical division of the data processing system. Furthermore, while the application programs 324, 325 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 9 but may be provided by other arrangements and/or divisions of functions between data processing systems. For example, although FIG. 9 is illustrated as having various circuits and modules, one or more of these circuits or modules may be combined or separated without departing from the scope of the present invention.

Figure 10:
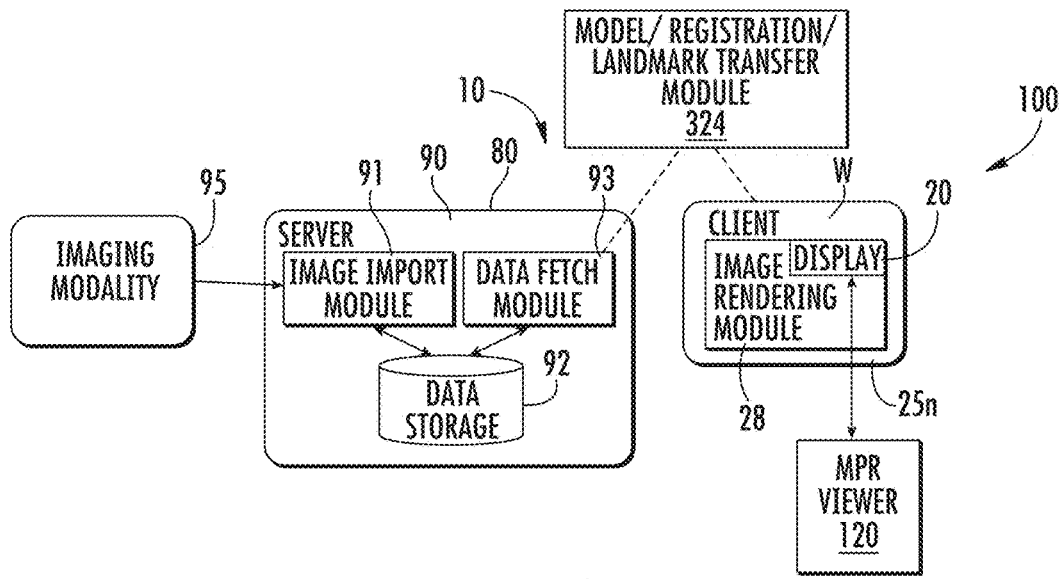
FIG. 10 is a schematic illustration of a system for providing the deformity measurements according to embodiments of the present invention.

FIG. 10 illustrates that, in particular embodiments, a system 10 can include or be in communication with a PACS (picture archiving and communication) system 80. The system 10 can include, for example, at least one server 90 with an image import module 91, data storage 92, and a data fetch module 93. The system 10 can include at least one (clinical) client (e.g., workstation) W and a rendering system 28. The system 10 can include a 3-D model, registration and landmark transfer module 324. The module 324 can be in communication with the server 90, held partially or totally on one or more servers, or held partially or totally onboard the workstation W. The module 324 can be provided as sub modules that are distributed over different servers or clients or may be provided as sub modules or subroutines on a respective server 90 or client W. The system 10 can optionally be in communication with at least one imaging modality 95 that electronically obtains respective volume data sets (which for medical uses is patient data sets) and can electronically transfer the data sets to the electronic storage 92.

The at least one server 90 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

A plurality of different clinical sites can be in communication with the server 90. The server 90 can receive and analyze multiple images of respective patients from the different sites 100 at any one time.

In some particular embodiments, the imaging modality 95 can be any desirable modality such as, but not limited to MRI, CT (computed tomography), fluoroscopy, ultrasound, and the like. The visualization system 10 may also operate to render images using data sets from more than one of these modalities. That is, the visualization system 10 may be configured to render images irrespective of the imaging modality data type (i.e., a common system may render images for both CT and MRI volume image data). In some embodiments, the system 10 may optionally combine image data sets generated from different imaging modalities 95 to generate a combination image for a patient.

The analysis system 10 can include at least one display or screen 20, typically onboard or in communication with a clinical site workstation W. It is noted that the terms "display" and "screen" are used interchangeably. As noted above, the display 20 can include a touch-input/touch-screen with a GUI 20c. The display 20 may be held on any type display and, indeed, more than one display, including, for example, an electronic notebook, smart phone, laptop computer, desktop computer or a workstation W.

Turning now to FIG. 11, a flow chart of exemplary operations that can be used to carry out embodiments of the invention is shown. A 3-D model of a spine with a plurality of defined landmarks in defined locations and different planes which may include each of an axial plane, sagittal plane and coronal (frontal) plane can be electronically provided or attached by a user (block 200).

A 3-D patient image of the spine can be electronically provided (block 205).

Subvolumes of the patient image data set and model can be extracted, each subvolume includes at least one vertebrae in full to be registered (T1-L5) and at least one neighboring upper and/or lower vertebrae or a portion thereof (block 210). The model and the patient image can be electronically registered (block 215). The registration can be carried out vertebrae-by-vertebrae instead of via an entire spine (e.g., over an entire or substantially entire spine volume). Landmarks from the model can be electronically transferred to the patient image after registration (block 220). Measurements of one or more of position, rotation and local deformity of each or selected vertebra can be electronically automatically generated using the transferred landmarks (block 225).

In some embodiments, an electronic library of different target organs with preset landmarks for different medical conditions can be electronically provided or accessed (block 202).

In some embodiments, an electronic library of different models of the spine with different preset landmarks for different medical conditions can be electronically provided or accessed (block 203).

In some embodiments, the 3-D model can be configured to allow a user to adjust the placement of one or more landmarks using an orthogonal MPR reconstruction viewer (block 201).

In some embodiments, the method can be carried out to electronically automatically place at least 16 spaced apart landmarks on each vertebrae in the model including landmarks 1-6 in an axial plane, landmarks 1-2 and 7-11 in the sagittal plane, and landmarks 3-4, 7-8 and 13-16 in the frontal plane (block 204).

The analysis methods may include electronically estimating an initial position and rotation of each vertebra for the patient data using spinal canal centerline extraction, disc detection and vertebral center point estimation (block 212).

The analysis methods may include electronically performing image enhancement to enhance (make them more visually dominant) structures separating adjacent vertebrae (block 212).

In some embodiments, the analysis methods can include generating a plurality of graphs of the spine with T1-L5 curvature with one or more calculated measurements.

The graphs of the calculated measurements can include at least one of: x (mm) vs. z, y (mm) vs. z, $\theta x$ v. z (degrees), $\theta y$ v. z (degrees) and $\theta z$ v. z (degrees) and $\xi$ (representing local deformity or lateral vertebral wedging) (block 228).

In some embodiments, the methods can include visually marking primary curvature with end vertebrae and apical vertebrae, with the end vertebrae defined by the vertebrae with maximal/minimal frontal rotation (block 229).

The generating can be provided in under 5 minutes from the obtaining step for the entire spinal vertebra (block 226).

In some embodiments, the analysis methods can include electronically analyzing spinal curvature and deformity using eigenvectors (block 227) which can be used to generate the graphs of (block 228), for example.

In summary, in particular embodiments, the vertebral measures are estimated from landmarks attached to the spine model and transferred to the patient data according to the registration result. The obtained measurements, describing the spinal deformity, can then be analyzed using PPC and CCA. As discussed above, the analysis of calculated measurements of curvature of 15 patients show that coronal rotation has a strong correlation with lateral displacement, axial rotation and deformation of the vertebra. In addition, sagittal rotation and anterior-posterior displacement is also strongly correlated.

Furthermore, the average PSE 0.9±0.9 mm suggests a very good fit of the deformed spine model. In fact, the PSE is slightly better than the results reported in Stern, D., Likar, B., Pernus, F. and Vrtovec, T.: 2011, Parametric modeling and segmentation of vertebral bodies in 3D CT and MR spine images, *Physics in Medicine and Biology* 56(23), 7505-7522; Klinder, T., Ostermann, J., Ehm, M., Franz, A., Kneser, R. and Lorenz, C.: 2009, Automated model-based vertebra detection, identification, and segmentation in CT images., *Medical Image Analysis* 13(3), 471-482.), 1.17±0.33 mm respectively 1.12±1.04 mm, where both are fully automatic methods for segmenting the vertebrae. Noteworthy in this context is also that both Stern et al. (2011) and Klinder et al. (2009) report rather extensive computation times, approximately 1 to 15 minutes per vertebra in (Stern et al. 2011) and close to 40 minutes for 12 vertebrae in (Klinder et al. 2009), to compare with a computation time of three to four minutes for 17 vertebrae according to embodiments of the present invention. Regarding the results in (Stern et al. 2011), it should also be pointed out that Stern et al. only estimate the PSE for a limited number of landmarks and that they only segment vertebral bodies. In addition, an advantage of the method in Klinder et al. 2009 is that that proposed method provides automatic identification of the vertebrae as well. Despite the low PSE, it should be noted that the errors are in general larger for the processes of the vertebrae, although the imperfect registration of the transverse processes appear to not affect the PSE in general. In addition, the thoracic vertebrae have in general a larger error, e.g. the lumbar vertebrae have an average PSE of 0.7-0.8 mm whereas the average PSE of the thoracic vertebrae range from 0.7 mm to 1.3 mm.

Comparing transferred landmarks and manually placed landmarks provides an average target registration error (TRE) of 2.3+/−1.7 mm. This is slightly better than the results (3.3±3.8 mm) reported by Delorme, S., Petit, Y., De Guise, J. A., Labelle, H., Aubin, C.-E. and Dansereau, J.: 2003, Assessment of the 3-D reconstruction and high-resolution geometrical modeling of the human skeletal trunk from 2-D radiographic images, *Biomedical Engineering, IEEE Transactions on* 50(8), 989-998, for evaluating the accuracy of using stereoradiography and reconstruction techniques for 3-D modeling of the vertebrae. Interestingly, the PSE suggests a much better registration accuracy than the TRE. The difference is believed to be due to the fact that corresponding landmarks are in general difficult to place in corresponding anatomical positions, and this can be even more difficult when one set of the landmarks are placed in patient data and the other set on a model. Thus, it is believed that the obtained TRE evidences that a suitable registration accuracy has been achieved.

Comparing the AVR as estimated from the transferred landmarks with corresponding manual measurements of the same, provides an average difference of 0.1±3.1°. This result can be compared with results previously reported. See, e.g., Adam, C. J. and Askin, G. N.: 2006, Automatic measurements of vertebral rotation in idiopathicscoliosis, *Spine: an international journal for the study of the spine* 31(3), E80-E83.; Vrtovec, T., Pernuš, F. and Likar, B.: 2010, Determination of axial vertebral rotation in MR images: comparison of four manual and a computerized method, *European Spine Journal* 19, 774-781; and Forsberg, D., Lundström, C., Andersson, M., Vavruch, L., Tropp, H. and Knutsson, H.: 2013, Fully automatic measurements of axial vertebral rotation for assessment of spinal deformity in idiopathic scoliosis, *Physics in Medicine and Biology* 58(6), 1775-1787. Three prior methods for computerized AVR measurements were evaluated and results of 0.25±3.8°, −0.3±1.3° and 0.7±4.2 were reported. Hence, the AVR noted above, when compared with the prior computerized and manual measurements, is on par with earlier reported results. Furthermore, the obtained variability is similar to the inter-observer variability, which was 0.1+/−2.4 for the observers included in this evaluation.

A significant advantage of the proposed method, compared to other computerized methods for rotational measurements, is that it does not rely on vertebral symmetry. In addition, the method is fully automatic, computationally efficient and can be readily adapted to other measures by changing the set of landmarks used.

Embodiments of the invention fit a detailed (substantially anatomically correct) spine model via image registration and the transfer of landmarks to patient data, for estimating the position, rotation and deformation of each vertebra in the spine. This is believed to provide great relevance for several diseases causing a deformation of the spinal curvature. While particularly suitable to evaluate patients for idiopathic scoliosis, a disease in need of better methods and measures for automatically quantifying and assessing the induced spinal deformity, embodiments of the invention can provide a useful tool for clinicians in their research or treatment related to idiopathic scoliosis, to explore underlying mechanisms of the disease, and in clinical work for determining the most suitable treatment for individual patients and tracking efficacy of treatment over time or progression of a spinal disease.

It is believed that the described methodologies have several advantages compared to other computerized methods. For example, compared to other methods assessing rotation (mainly axial vertebral rotation), embodiments of the invention do not rely on the symmetry of the vertebral body for measuring the rotation of the vertebral body. In addition, it can be fully automatic. It is also believed that the GPU can be used for executing various computations thereby providing a computation time of about three minutes for all 17 levels of the spine, given the current implementation. Compared to stereoradiography and 3D reconstruction it has the benefit of not requiring a dedicated imaging modality but can be used with standard CT.

The obtained measurements can be analyzed to gain further understanding of idiopathic scoliosis such as the dependence between the different measures, a novel approach compared to earlier research that primarily focus on clustering of sub-types of idiopathic scoliosis based upon multiple measures. See, e.g., L. Duong, F. Cheriet, and H.

Labelle. Three-dimensional classification of spinal deformities using fuzzy clustering. *Spine,* 31(8):923-930, 2006; S. Kadoury and H. Labelle. Classification of three-dimensional thoracic deformities in adolescent idiopathic scoliosis from a multivariate analysis. *European Spine Journal,* 21(1):40-49,2012; and A. P. Sangole, C. E. Aubin, H. Labelle, I. A. F. Stokes, L. G. Lenke, R. Jackson, and P. Newton. Three-dimensional classification of thoracic scoliotic curves. *Spine,* 34(1):91-99, 2008.

The results of the combined PCA and CCA analysis show, for example, that the strongest linear dependence is between the lateral displacement and the frontal rotation of the vertebra. That there is a strong linear dependence between these two measures is well in-line with what is previously known. However, other interesting conclusions can be drawn by comparing the different pair-wise linear dependencies, since this analysis can indicate which measures that are the most relevant for describing a scoliotic curvature.

For instance, the fact that the strongest linear relationships exist between the pair-wise measures x—$\theta_Y$, y—$\theta_X$, $\theta_Y$–$\theta_Z$ and $\theta_Y$–$\xi$, indicates that it suffices to measure the frontal rotation $\theta_Y$ and the sagittal rotation $\theta_X$ for describing a scoliotic curvature. Or rather, that these two measures can be considered to carry sufficient information to describe the other measures as well. This hypothesis is further supported by the pair-wise estimates with a low MI. Note though, that this hypothesis is in stark contrast with the previously mentioned understanding of axial vertebral rotation as an important discriminate feature of idiopathic scoliosis. However, given the limited number of included patients, further analysis including more patients is called for before any conclusion can be made.

The deformation measure, which can be calculated as the lateral vertebral height difference (corresponding to lateral vertebral wedging), could for instance instead be defined as the angle between the planes fitted to the superior and inferior endplates. Note that measurements were performed using this latter definition, but the angular difference between the endplates associated with the anterior-posterior vertebral wedging is much larger than the angular difference related to the lateral vertebral wedging, which made it difficult to analyze effects of lateral vertebral wedging. Another aspect is to determine how to decompose the estimated rotation matrix. While Euler angles with a fixed world frame were described above, there exist a number of alternatives for this decomposition.

In summary, automated analysis of patient image data can be carried out to estimate position, rotation and deformation of each vertebrae in the spine. The methods are not limited to the current set of landmarks, which can be exchanged for a different set of landmarks providing an analysis methodology that is adaptable.

Embodiments of the invention describe a novel scheme for analyzing the dependence between different measures related to idiopathic scoliosis.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of providing automated measurements associated with anatomical features of a spine, comprising:
   electronically providing a three dimensional (3-D) model of the spine having substantially naturally shaped vertebrae, with a plurality of landmarks electronically applied to each of the vertebrae;
   obtaining 3-D patient image data of a spine of the patient;
   extracting subvolumes of the 3-D patient image data associated with the spine, respective subvolumes each including at least one vertebra in full and at least one neighboring vertebrae structure or a portion thereof;
   extracting subvolumes of the 3-D model corresponding to the subvolumes of the patient image data;
   electronically registering, subvolume by subvolume, the 3-D model and the 3-D patient image data of the spine; then
   electronically transferring the landmarks from the model to the 3-D patient image; and
   electronically calculating measurements for one or more vertebrae, including at least one of the following: (i) position in x, y and z coordinates (mm), (ii) rotation $\theta x$, $\theta y$, $\theta z$ in degrees, and (iii) a local deformity (lateral wedge) value (mm) using the transferred landmarks.

2. The method of claim 1, further comprising electronically visually increasing and/or resolving respective vertebra features in the subvolumes of the 3-D patient image data to enhance those features relative to an unenhanced state before electronically registering corresponding subvolumes of the model and the patient image data.

3. The method of claim 1, wherein each vertebra comprises discrete and spaced apart landmarks associated with an axial plane, discrete and spaced apart landmarks associated with a sagittal plane and discrete and spaced apart landmarks associated with a coronal plane.

4. The method of claim 1, wherein the registration is carried out by first applying an affine registration for each vertebra, then applying a deformable registration for each vertebra.

5. The method of claim 1, wherein, before the registration, the method comprises pre-processing the patient image data to electronically estimate an initial position and rotation of each vertebrae of the patient image data by (i) calculating a spinal canal centerline, detecting disc location, (ii) calculating an initial rotation, then (iii) calculating an estimate of vertebrae center points, then (iv) adjusting vertebral rotation using the estimated center points and generating an adjusted estimated spine shape with an estimated location and rotation of the respective vertebrae of the patient data using the adjusted estimated rotation.

6. The method of claim 1, further comprising electronically generating a plurality of graphs of T1-L5 curvature using the calculated measurements, including graphs of displacement (mm) x vs. z and y vs. z, a graph of the calculated local deformity (mm) vs. z and at least one graph of a respective rotational measurement of one or more of rotation $\theta x$, $\theta y$, and $\theta z$ in degrees vs. z.

7. The method of claim 1, wherein the x, y and z coordinates of each vertebrae are calculated using an average of coordinates of the transferred landmarks of a respective vertebrae.

8. The method of claim 1, wherein rotation $\theta x$, $\theta y$, $\theta z$ in degrees are calculated as Euler angles, using a fixed world frame, derived from rotation matrix $R = R_Z(\theta_Z)R_Y(\theta_Y)R_X(\theta_X)$, wherein: $\theta_Z$ corresponds to axial vertebral rotation, $\theta_Y$ to frontal rotation and $\theta_X$ sagittal rotation.

9. The method of claim 1, wherein the local deformity is electronically calculated based on a vertebral height difference of vertebral height measurements between defined pairs of landmarks.

10. The method of claim 1, wherein the local deformity is electronically calculated non-invasively based on an angle between planes fitted to superior and inferior endplates using the patient image data and the transferred landmarks.

11. The method of claim 1, further comprising electronically generating graphs that illustrate a primary curvature that is defined with visually marked end vertebrae and an apical vertebrae with the end vertebrae defined by maximal and minimal frontal rotation θy.

12. The method of claim 11, further comprising electronically generating an estimated Cobb angle using the calculated measurements.

13. The method of claim 1, further comprising electronically generating statistical models of spinal curvature of groups of different 3-D patient image data using Eigenvector analysis of the calculated measurements.

14. The method of claim 1, further comprising evaluating whether a patient has idiopathic scoliosis and/or for quantifying an extent or configuration of the idiopathic scoliosis based on the calculated measurements.

15. The method of claim 1, wherein the electronic transfer of the landmarks is carried out using an electronically calculated estimated transformation that can evaluate both symmetric and asymmetric vertebrae of the 3-D patient image data.

16. The method of claim 1, wherein the electronically registering is carried out using phase-based registration.

17. The method of claim 1, wherein the electronically providing the 3-D model of the spine having substantially naturally shaped vertebrae has vertebrae at all levels, T1-L5.

18. The method of claim 1, wherein the method further comprises allowing a user to electronically define placement of the landmarks on the 3-D model using a GUI and display presenting the 3-D model.

19. The method of claim 1, wherein the electronically providing the 3-D model of the spine having substantially naturally shaped vertebrae with the landmarks is carried out by providing a menu of selectable landmark sets and allowing a user to select one or more of the landmark sets for use.

20. The method of claim 1, wherein the electronically providing the 3-D model of the spine having substantially naturally shaped vertebrae with the landmarks is carried out by providing the 3-D model with a default set of landmarks.

21. The method of claim 20, further comprising allowing a user to electronically adjust location of landmarks and/or add or remove one or more landmarks.

22. The method of claim 1, wherein the electronically providing the 3-D model of the spine having substantially naturally shaped vertebrae with the landmarks is carried out by providing a first landmark set for a first set of the calculated measurements and a second landmark set for a second set of calculated measurements, and wherein the first and second landmark sets comprise a plurality of spaced apart discrete landmarks placed about a boundary of the vertebrae and with a plurality of spaced apart landmarks in an axial plane, a plurality of the landmarks in a sagittal plane and a plurality of the landmarks in a coronal plane.

23. The method of claim 1, wherein the patient images are time-resolved images for generating visual output of curvature change over time thereby allowing monitoring of progression of a disease, change associated with a therapy and providing visualizations and associated calculated measurements associated with changes in spinal structure between images taken in different positions of a patient.

24. A clinician workstation comprising:
at least one display; and
a circuit in communication with the at least one display, the circuit comprising or in communication with at least one processor configured to:
provide a three dimensional (3-D) model of the spine having substantially naturally shaped vertebrae, with a plurality of landmarks electronically applied to each of the vertebrae and/or which allows a user to electronically apply landmarks to one or more vertebrae of the 3-D model;
obtain 3-D patient image data of a spine of the patient;
extract subvolumes of the 3-D patient image data associated with the spine, respective subvolumes each including at least one vertebra in full and at least one neighboring vertebrae structure or a portion thereof;
extract subvolumes of the 3-D model corresponding to the subvolumes of the patient image data;
register, subvolume by subvolume, the 3-D model and the 3-D patient image data of the spine; then
transfer the landmarks from the model to the 3-D patient image; and
calculate measurements for one or more vertebrae, including at least one of the following: (i) position in x, y and z coordinates (mm), (ii) rotation θx, θy, θz in degrees, and (iii) a local deformity (lateral wedge) value (mm) using the transferred landmarks.

25. The workstation of claim 24, wherein the at least one processor is configured to register, subvolume by subvolume, the 3-D model and the 3-D patient image data of the spine by (i) first applying an affine registration for each vertebra, then (ii) applying a deformable registration for each vertebra.

26. The workstation of claim 24, wherein the at least one processor of the circuit is configured to pre-process the 3-D patient image data to estimate an initial position and rotation of each vertebrae of the patient image data by (i) calculating a spinal canal centerline, detecting disc location, (ii) calculating an initial rotation, then (iii) calculating an estimate of vertebrae center points, then (iv) adjusting vertebral rotation using the estimated center points and generating an adjusted estimated spine shape with an estimated location and rotation of the respective vertebrae of the patient data using the adjusted estimated rotation, and wherein the at least one processor is configured to register the 3-D model and the 3-D patient image data of the spine using the generated adjusted estimated spine shape.

27. The workstation of claim 24, wherein the at least one processor of the circuit is configured to generate a plurality of graphs that illustrate a primary curvature that is defined with visually marked end vertebrae and an apical vertebrae with the end vertebrae defined by maximal and minimal frontal rotation θy.

28. The workstation of claim 24, wherein the at least one processor of the circuit is configured to generate an estimated Cobb angle using the calculated measurements.

29. The workstation of claim 24, wherein the patient images are time-resolved images, and wherein the at least one processor of the circuit is configured to generate visual output of graphs of change in curvature over time thereby allowing monitoring of progression of a disease, change associated with a therapy and providing visualizations and associated calculated measurements associated with changes in spinal structure between images taken in different positions of a patient.

30. The workstation of claim 24, wherein the at least one processor generates a plurality of graphs of T1-L5 curvature using the calculated measurements, including graphs of displacement (mm) x vs. z and y vs. z, a graph of the calculated local deformity (mm) vs. z and at least one graph of a respective rotational measurement of one or more of rotation θx, θy, and θz in degrees vs. z.

31. The workstation of claim 24, wherein the electronically applied landmarks of the 3-D model comprises at least four spaced apart discrete landmarks including landmarks on perimeters of the vertebrae with a plurality of spaced apart landmarks in an axial plane, a plurality of the landmarks in a sagittal plane and a plurality of the landmarks in a coronal plane.

32. A system for evaluating spinal patient image data, comprising:
 at least one processor comprising a spinal deformity analysis module; and
 at least one display in communication with the at least one processor,
 wherein the spinal deformity analysis module is configured to:
  provide a three dimensional (3-D) model of the spine having substantially naturally shaped vertebrae to the display, the 3-D model (i) is configured to allow a user to electronically apply landmarks to one or more vertebrae of the 3-D model and/or (ii) has a plurality of landmarks electronically pre-applied to each of the vertebrae of the 3-D model;
  obtain 3-D patient image data of a spine of the patient;
  register the 3-D model and the 3-D patient image data of the spine; then
  transfer the landmarks from the model to the 3-D patient image;
  calculate measurements for the vertebrae, including a plurality of the following: (i) position in x, y and z coordinates (mm), (ii) rotation θx, θy, θz in degrees, and (iii) a local deformity (lateral wedge) value (mm) using the transferred landmarks; and
  generate a plurality of graphs of curvature of the spine to the display using the calculated measurements.

33. The system of claim 32, wherein the electronically applied landmarks of the 3-D model comprises at least four spaced apart discrete landmarks including landmarks on perimeters of the vertebrae with a plurality of spaced apart landmarks in an axial plane, a plurality of the landmarks in a sagittal plane and a plurality of the landmarks in a coronal plane.

34. The system of claim 32, wherein the spinal deformity analysis module generates a plurality of graphs of T1-L5 curvature using the calculated measurements, including graphs of displacement (mm) x vs. z and y vs. z, a graph of the calculated local deformity (mm) vs. z and at least one graph of a respective rotational measurement of one or more of rotation θx, θy, and θz in degrees vs. z.

35. A computer program product for analyzing image data sets, the computer program product comprising:
 a non-transitory computer readable storage medium having computer readable program code embodied in the medium, the computer-readable program code comprising:
 computer readable program code configured to:
  provide a three dimensional (3-D) model of the spine having substantially naturally shaped vertebrae, with a plurality of landmarks electronically applied to each of the vertebrae;
  obtain 3-D patient image data of a spine of the patient;
  extract subvolumes of the 3-D patient image data associated with the spine, respective subvolumes each including at least one vertebra in full and at least one neighboring vertebrae structure or a portion thereof;
  extract subvolumes of the 3-D model corresponding to the subvolumes of the patient image data;
  register, subvolume by subvolume, the 3-D model and the 3-D patient image data of the spine; then
  transfer the landmarks from the model to the 3-D patient image; and
  calculate measurements for one or more vertebrae, including at least one of the following: (i) position in x, y and z coordinates (mm), (ii) rotation θx, θy, θz in degrees, and (iii) a local deformity (lateral wedge) value (mm) using the transferred landmarks.

* * * * *

UNITED STATES PATENT AND TRADEMARK OFFICE
CERTIFICATE OF CORRECTION

PATENT NO. : 9,561,004 B2
APPLICATION NO. : 14/013189
DATED : February 7, 2017
INVENTOR(S) : Daniel Forsberg It is certified that error appears in the above-identified patent and that said Letters Patent is hereby corrected as shown below:

In the Specification

Column 22, Lines 46 and 47: Please correct "and $x_i=[x_i \ x_2 \ldots x_p]^T$,"
to read -- and $\mathbf{x}_i = [x_1 \ x_2 \ \cdots x_p]^T$, --

Column 22, Line 47: Please correct "n measurements of p"
to read -- $n$ measurements of $p$ --

Signed and Sealed this
Eighth Day of August, 2017

Joseph Matal
Performing the Functions and Duties of the
Under Secretary of Commerce for Intellectual Property and
Director of the United States Patent and Trademark Office